United States Patent
Watanabe et al.

(10) Patent No.: US 6,841,693 B1
(45) Date of Patent: Jan. 11, 2005

(54) TRANSITION METAL COMPOUND, OLEFIN POLYMERIZATION CATALYST, AND METHOD OF POLYMERIZING OLEFIN

(75) Inventors: Masami Watanabe, Ichihara (JP); Haruhito Sato, Ichihara (JP); Masahiko Kuramoto, Ichihara (JP); Shinji Tanaka, Tokuyama (JP); Takao Tamura, Tokuyama (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 270 days.

(21) Appl. No.: 10/111,419

(22) PCT Filed: Nov. 10, 2000

(86) PCT No.: PCT/JP00/07942

§ 371 (c)(1),
(2), (4) Date: May 7, 2002

(87) PCT Pub. No.: WO01/36379

PCT Pub. Date: May 25, 2001

(30) Foreign Application Priority Data

Nov. 11, 1999 (JP) .......................... 11-320448
Nov. 30, 1999 (JP) .......................... 11-340219

(51) Int. Cl.$^7$ .................... C07F 15/00; C08F 4/70; B01J 31/00

(52) U.S. Cl. .................. 556/32; 556/137; 556/138; 502/103; 502/117; 502/167; 526/115; 546/2

(58) Field of Search ............... 556/32, 137, 138; 502/103, 117, 167; 526/115; 546/2

(56) References Cited

U.S. PATENT DOCUMENTS 6,200,925 B1    3/2001    Ponasik, Jr. et al. ........ 502/167

FOREIGN PATENT DOCUMENTS

WO    98/27124    6/1998

OTHER PUBLICATIONS

Mahapatra, Bipin B. et al., "Polymetallic complexes. Part–XLII. Complexes of cobalt–, nickel–, copper–, zinc–, cadmium– and mercury (II) with a ONNO donor azo dye, 4,4'–bis(ethyl cyanoacetate–2'–azo)diphenyl", J. Indian Chem. Soc., 1995, vol. 72 No. 5, pp. 347–348.

Primary Examiner—Mark L. Bell
Assistant Examiner—J. Pasterczyk
(74) Attorney, Agent, or Firm—Oblon, Spivak, McClelland, Maier & Neustadt, P.C.

(57) ABSTRACT

A transition metal compound of Groups to 10 of the Periodic Table, represented by the following formula (1):

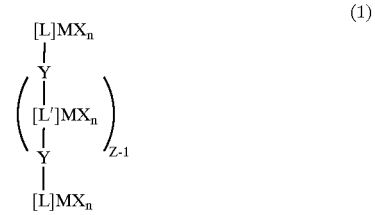

wherein M represents a transition metal of Groups 8 to 10 of the Periodic Table; L, electrically neutral, represents a hetero atom-containing hydrocarbon group represented by the following formula (2)

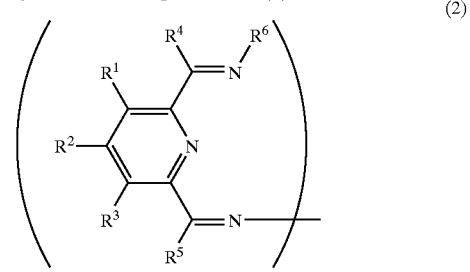

wherein $R^1$ to $R^5$ each independently represent a hydrogen atom, a halogen atom, a hydrocarbon group having form 1 to 20 carbon atoms, a halogenohydrocarbon group having from 1 to 20 carbon atoms, or a hetero atom-containing group, and optionally these groups are bonded to each other to form a ring; $R^6$ represents a hydrogen atom, a hydrocarbon group having form 1 to 40 carbon atoms, a halogenohydrocarbon group having from 1 to 40 carton atoms, or a hetero atom-containing group;

L' electrically neutral, represents a hetero atom-containing hydrocarbon group represented by the following formula (3)

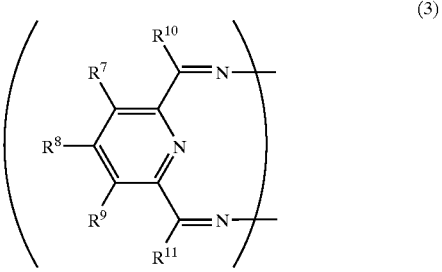

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring;

X represents a covalent-bonding or ionic-bonding group, and a plurality of X's are the same or different; Y represents an aromatic group-containing crosslinking group; Z is an integer of 1 or more, indicating the degree of polymerization of the compound; n indicates the atomic valency of M; and each of M, L, and Y are the same or different.

14 Claims, No Drawings

OTHER PUBLICATIONS

Fleischer, Everly B. et al., "Linked porphyrin systems", J. Heterocycl. Chem., 1991, vol. 28 No. 7, pp. 1693–1699.

Palmer, Brian D. et al., "Synthesis, DNA binding interactions and biological activity of bis–platinum (II) complexes of N, N, N', N'–tetrakis (2–aminoethyl) diamines", Anti–Cancer Drug Des., 1992, vol. 7 No. 5, pp. 385–401.

Small, Brooke L. et al., "Polymerization of Propylene by a New Generation of Iron Catalysts: Mechanisms of Chain Initiation, Propagation, and Termination", Macromolecules, 1999, vol. 32 No. 7, pp. 2120–2130.

TRANSITION METAL COMPOUND, OLEFIN POLYMERIZATION CATALYST, AND METHOD OF POLYMERIZING OLEFIN

TECHNICAL FIELD

The present invention relates to a novel transition metal compound to give a catalyst for efficiently and inexpensively producing polyolefins and α-olefins, to an olefin polymerization catalyst comprising the transition metal compound, and to an olefin polymerization method. The invention also relates to a novel transition metal compound to give a catalyst for producing α-olefins with reduced formation of side products such as heavy matters, waxy matters and others, to an olefin polymerization catalyst comprising the transition metal compound and to an olefin polymerization method.

RELATED ART

Heretofore, Ziegler-Natta catalysts have been known from the past for olefin polymerization catalysts for producing polyolefins. The technical innovation in the art is now remarkable, as will be seen in the recent development of metallocene catalysts, and it has significant influences on the industrial field. Further developing next-generation catalysts is much desired these days.

On the other hand, known is a process (SHOP; Shell Higher Olefin Process) of using a nickel complex for polymerizing ethylene to produce ethylene oligomers (often referred to as α-olefins), but the process is problematic in that the activity of the nickel complex used therein is low. Recently, it has been found that a catalyst comprising a nickel-diimine complex (International Patent Laid-Open No. 96-23010) and a catalyst comprising an iron or cobalt chelated complex (Chem. Commun., 1998, 849–850; J. Am. Chem. Soc., 1998, 120, 7143–7144; J. Am. Chem. Soc., 1998, 120, 4049–4050) have high activity for ethylene polymerization. For example, it is said that, in a method of using an iron chelated complex as a main catalyst combined with methylaluminoxane as a promoter for ethylene polymerization, the catalyst exhibits high ethylene polymerization activity with good terminal selectivity in producing ethylene oligomers. In addition, International Patent Laid-Open Nos. 98-27124, 99-02472 and 99-12981 disclose a method of polymerizing ethylene in the presence of a complex similar to the above. However, these methods are all defective in that they require a large amount of an expensive aluminoxane and give side products, polymers and waxes in large quantities. Anyhow, at present, no one knows an efficient method for producing α-olefins in which the unit activity of the catalyst used is high and the amount of side products such as heavy matters, waxy matters and others formed is reduced. On the other hand, regarding compounds of transition metals of Group 8 of the Periodic Table, Japanese Patent Laid-Open Nos. 96215/1989, 96216/1989 and 96217/1989 disclose a method for producing chelate complexes comprising iron and a hetero atom-containing hydrocarbon group. However, these compounds produced therein are for ferromagnetic films.

The present invention has been made in consideration of the above-mentioned viewpoints, and its object is to provide an olefin polymerization catalyst having high activity for olefin polymerization, to provide a transition metal compound to give the catalyst, and to provide an olefin polymerization method.

In addition, the invention is also to provide an olefin polymerization catalyst for producing α-olefins with reduced formation of side products such as heavy matters, waxy matters and others, to provide a transition metal compound to give the catalyst, and to provide an olefin polymerization method.

DISCLOSURE OF THE INVENTION

We, the present inventors have assiduously studied so as to attain the objects as above, and, as a result, have found that a specific transition metal compound of the Groups 8 to 10 of the Periodic Table, and an olefin polymerization catalyst that comprises the transition metal compound along with at least one selected from organoaluminium compounds, ionic compounds, Lewis acids, and clay, clay minerals and ion-exchanging layered compounds can effectively attain the objects. On the basis of these findings, we have completed the present invention.

Specifically, the invention is summarized as follows:

1. A transition metal compound of Groups 8 to 10 of the Periodic Table, represented by the following general formula (1):

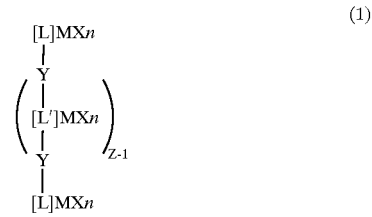

wherein M represents a transition metal of Groups 8 to 10 of the Periodic Table; L and L' each represent a hetero atom-containing hydrocarbon group; X represents a covalent-bonding or ionic-bonding group, and a plurality of X's, if any, may be the same or different; Y represents an aromatic group-containing crosslinking group; Z is an integer of 1 or more, indicating the degree of polymerization of the compound; n indicates the atomic valency of M; and M, L, and Y may be the same or different.

2. The transition metal compound of above 1, wherein [L] is represented by the following general formula (2):

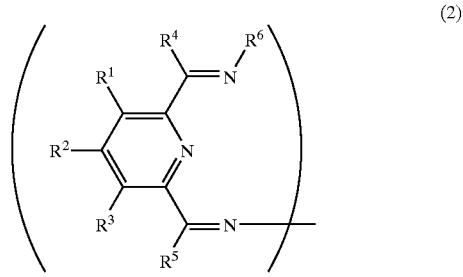

wherein $R^1$ to $R^5$ each independently represent a hydrogen atom, a halogen atom, a hydrocarbon group having from 1 to 20 carbon atoms, a halogenohydrocarbon group having from 1 to 20 carbon atoms, or a hetero atom-containing group, and these may be bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group.

3. The transition metal compound of above 1, wherein [L'] is represented by the following general formula (3):

(3)

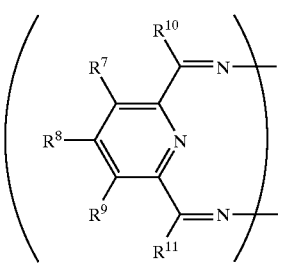

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and these may be bonded to each other to form a ring.

4. A transition metal compound of the following general formula (4)

(4)

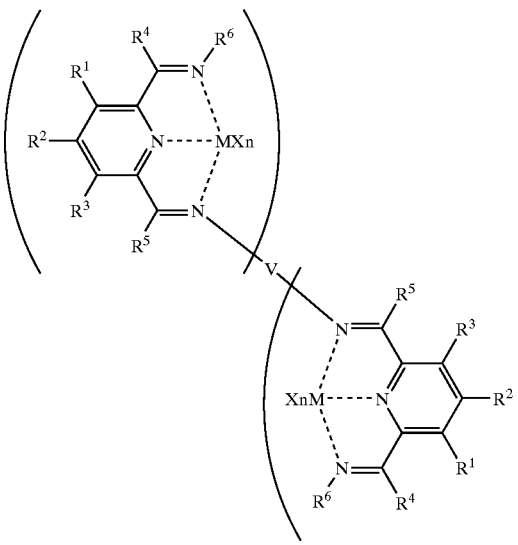

wherein V is a crosslinking group to be represented by the following general formula (5A) or (5B):

(5A)

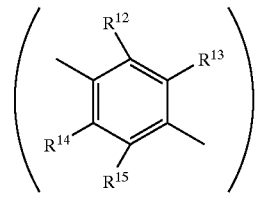

(5B)

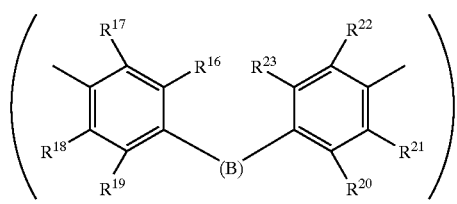

M represents a transition metal of Groups 8 to 10 of the Periodic Table; $R^1$ to $R^5$ each independently represent a hydrogen atom, a halogen atom, a hydrocarbon group having from 1 to 20 carbon atoms, a halogenohydrocarbon group having from 1 to 20 carbon atoms, or a hetero atom-containing group, and these may be bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group; X represents a covalent-bonding or ionic-bonding group, and a plurality of X's, if any, maybe the same or different; n indicates the atomic valency of M; $R^{12}$ to $R^{15}$, and $R^{16}$ to $R^{23}$ each independently represent a hydrogen atom (except for $R^{18}$ and $R^{21}$), or a hydrocarbon group having from 1 to 20 carbon atoms, and these may be the same or different; $R^{16}$ and $R^{23}$ may be bonded to each other to form a ring; B represents —$(R^{24}_2C)_m$—, —$R^{24}_2Si$—, —O—, —S—, or —$R^{24}N$—; $R^{24}$ represents a hydrogen atom, or a hydrocarbon group having from 1 to 20 carbon atoms; and m is an integer of from 0 to 4.

5. The transition metal compound of above 4, wherein $R^{12}$ and $R^{15}$ each are a hydrocarbon group having from 1 to 20 carbon atoms, and $R^{13}$ and $R^{14}$ are both hydrogen atoms.

6. The transition metal compound of above 4, wherein $R^6$ is a group to be represented by the following formula:

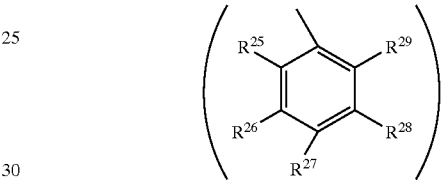

wherein $R^{26}$ to $R^{29}$ each independently represent a hydrogen atom; and $R^{25}$ is a methyl group, ethyl group or a hydrogen atom.

7. The transition metal compound of above 1 to 4, wherein the transition metal M is iron or cobalt.

8. An olefin polymerization catalyst comprising the following (A) and (B):
  (A) a transition metal compound that contains a transition metal of Groups 8 to 10 of the Periodic Table, at least two, hetero atom-containing hydrocarbon groups, and a crosslinking group;
  (B) at least one compound selected from a compound group of (B-1) organoaluminium compounds, (B-2) ionic compounds capable of being converted into cationic transition metal compounds through reaction with the transition metal compound, (B-3) Lewis acids, and (B-4) clay, clay minerals and ion-exchanging layered compounds.

9. An olefin polymerization catalyst comprising the following (A), (B) and (C):
  (A) a transition metal compound that contains a transition metal of Groups 8 to 10 of the Periodic Table, at least two, hetero atom-containing hydrocarbon groups, and a crosslinking group;
  (B) at least one compound selected from a compound group of (B-1) organoaluminium compounds, (B-2) ionic compounds capable of being converted into cationic transition metal compounds through reaction with the transition metal compound, (B-3) Lewis acids, and (B-4) clay, clay minerals and ion-exchanging layered compounds;
  (C) an organometallic compound.

10. The olefin polymerization catalyst of above 8 or 9, wherein the component (A) is the transition metal compound of above 1 to 7.

11. The olefin polymerization catalyst of above 8 or 9, wherein the component (B) is any of alkylaluminoxanes, boron compounds and phyllosilicic acid compounds.

12. A method for olefin polymerization, which comprising polymerizing an olefin in the presence of the olefin polymerization catalyst of above 8 or 9.

DETAILED DESCRIPTION OF THE INVENTION

The invention provides the above-mentioned transition metal compound, olefin polymerization catalyst and olefin polymerization method. The invention is described in detail hereinunder.

1. Transition Metal Compound

The transition metal compound of the invention is represented by the following formula (1):

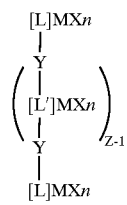

(1)

wherein M represents a transition metal of Groups 8 to 10 of the Periodic Table; L and L' each represent a hetero atom-containing hydrocarbon group; X represents a covalent-bonding or ionic-bonding group, and a plurality of X's, if any, may be the same or different; Y represents an aromatic group-containing crosslinking group; Z is an integer of 1 or more, indicating the degree of polymerization of the compound; n indicates the atomic valency of M; and M, L, and Y may be the same or different.

In the formula, M represents a transition metal of Groups 8 to 10 of the Periodic Table, and is preferably iron, cobalt, palladium or nickel. L represents a hetero atom-containing hydrocarbon group, concretely including an oxygen-containing hydrocarbon group (alkoxy group, etc.), a nitrogen-containing hydrocarbon group (amino group, imino group, etc.), a silicon-containing hydrocarbon group (silyl group represented by —SiR$_3$, etc.), etc. Preferably, it is a nitrogen-containing hydrocarbon group. X represents a covalent-bonding or ionic-bonding group, and a plurality of X's, if any, may be the same or different. Specific examples of X are a hydrogen atom, a halogen atom, a hydrocarbon group having from 1 to 20 (preferably from 1 to 10) carbon atoms, an alkoxy group having from 1 to 20 (preferably from 1 to 10) carbon atoms, an amino group, a phosphorus-containing group having from 1 to 20 (preferably from 1 to 12) carbon atoms (e.g., diphenylphosphino group), a silicon-containing group having from 1 to 20 (preferably from 1 to 12) carbon atoms (e.g., trimethylsilyl or trimethylsilylmethyl group), and a halogen-containing boron anion (e.g., BF$_4^-$). Of these, preferred are a halogen atom, and a hydrocarbon group having from 1 to 20 carbon atoms. The halogen atom includes fluorine atom, chlorine atom, bromine atom and iodine atom. Of those, preferred is chlorine atom. Y indicates an aromatic group-containing crosslinking group. Concretely, it is a divalent aromatic hydrocarbon group, such as an arylene group having from 6 to 20 carbon atoms. The arylene group having from 6 to 20 carbon atoms includes, for example, a phenylene group, a tolylene group, a xylylene group, a naphthylene group, a methylnaphthylene group, etc. Z is an integer of 1 or more, indicating the degree of polymerization of the compound. Z may fall between 1 and 1000, but preferably between 1 and 100, more preferably between 1 and 10, and most preferably 1. n indicates the atomic valency of M, concretely falling between 0 and 3.

In the transition metal compound of the invention, it is desirable that [L] is represented by the following general formula (2):

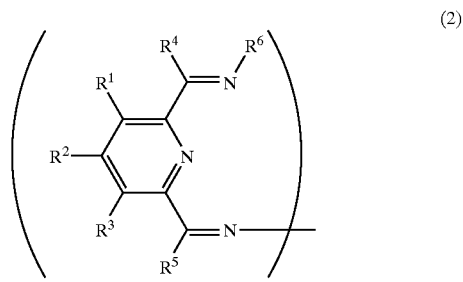

(2)

wherein $R^1$ to $R^5$ each independently represent a hydrogen atom, a halogen atom, a hydrocarbon group having from 1 to 20 carbon atoms, a halogenohydrocarbon group having from 1 to 20 carbon atoms, or a hetero atom-containing group, and these may be bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group.

In the formula, $R^1$ to $R^5$ each independently represent a hydrogen atom, a halogen atom, a hydrocarbon group having from 1 to 20 carbon atoms, a halogenohydrocarbon group having from 1 to 20 carbon atoms, or a hetero atom-containing group, and these may be bonded to each other to form a ring. The halogen atom includes fluorine atom, chlorine atom, bromine atom and iodine atom. The hydrocarbon group having from 1 to 20 carbon atoms includes, for example, a linear or branched alkyl group having from 1 to 20 carbon atoms, a cycloalkyl group having from 3 to 20 carbon atoms, an aryl group having from 6 to 20 carbon atoms, an arylalkyl group having from 7 to 20 carbon atoms, etc. Concretely, the linear or branched alkyl group having from 1 to 20 carbon atoms includes a methyl group, an ethyl group, an n-propyl group, an isopropyl group, an n-butyl group, an isobutyl group, a sec-butyl group, a tert-butyl group, all types of pentyl groups, all types of hexyl groups, all types of octyl groups, all types of decyl groups, all types of tetradecyl groups, all types of hexadecyl groups, all types of octadecyl groups, etc. The cycloalkyl group having from 3 to 20 carbon atoms includes, for example, a cyclopentyl group, a cyclohexyl group, a cyclooctyl group, etc. The ring of the cycloalkyl group may have some substituent such as a lower alkyl group or the like introduced thereinto. The aryl group having from 6 to 20 carbon atoms includes, for example, a phenyl group, a tolyl group, a xylyl group, a naphthyl group, a methylnaphthyl group, etc. The arylalkyl group having from 7 to 20 carbon atoms includes, for example, a benzyl group, a phenethyl group, etc. The halogenohydrocarbon group having from 1 to 20 carbon atoms is one formed by halogenating a hydrocarbon group having from 1 to 20 carbon atoms such as that mentioned above.

The hetero atom-containing group includes, for example, —OR, —SR, and —NR$_2$. R represents a hydrocarbon group having from 1 to 20 carbon atoms. For the hydrocarbon group having from 1 to 20 carbon atoms, referred to are those mentioned herein above for the groups $R^1$ to $R^5$.

R⁶ represents a hydrogen atom, a hydrocarbon group having from 1 to 40 carbon atoms, a halogenohydrocarbon group having from 1 to 40 carbon atoms, or a hetero atom-containing group. For the hydrocarbon group having from 1 to 40 carbon atoms and the halogenohydrocarbon group having from 1 to 40 carbon atoms, referred to are those concretely mentioned herein above for the hydrocarbon group having from 1 to 20 carbon atoms and the halogenohydrocarbon group having from 1 to 20 carbon atoms. In addition to these, further mentioned are hydrocarbon groups of the above-mentioned hydrocarbon or halogenohydrocarbon group having from 1 to 20 carbon atoms and having any of the above-mentioned, linear or branched alkyl group having from 1 to 20 carbon atoms, cycloalkyl group having from 3 to 20 carbon atoms, aryl group having from 6 to 20 carbon atoms or arylalkyl group having from 7 to 20 carbon atoms, bonded thereto. For the hetero atom-containing group, referred to are the same as those mentioned herein above. R⁶ is preferably an aryl group having from 6 to 40 carbon atoms. Concretely, it includes a hydrocarbon group containing any of a phenyl group, a tolyl group, a xylyl group, a naphthyl group, a methylnaphthyl group, etc. Especially preferably, R⁶ is a group represented by the following general formula:

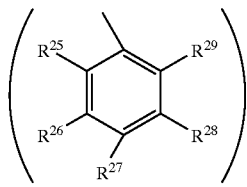

wherein $R^{26}$ to $R^{29}$ each independently represent a hydrogen atom; and $R^{25}$ is a methyl group, ethyl group or a hydrogen atom, as the compound is effective for inhibiting the formation of heavy matters and waxy matters.

In the transition metal compound of the invention, [L'] is preferably represented by the following general formula (3):

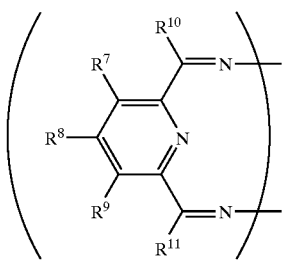

(3)

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and these may be bonded to each other to form a ring.

In the formula, $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and these may be bonded to each other to form a ring. The halogen atom includes fluorine atom, chlorine atom, bromine atom and iodine atom. For the hydrocarbon group having from 1 to 20 carbon atoms and the halogenohydrocarbon group having from 1 to 20 carbon atoms, referred to are those mentioned herein above for the groups $R^1$ to $R^5$.

Concretely, the transition metal compound of the invention includes the compounds of the above-mentioned general formula (4).

In case where V in formula (4) is represented by the following general formula (5A):

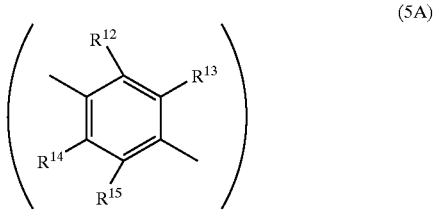

(5A)

M, X, n, $R^1$ to $R^5$ and $R^6$ in that formula (4) may have the same meanings as those in formulae (1) and (2). More preferably, however, X in formula (4) is a monovalent anion, even more preferably selected from a halogen atom and an alkyl group. In formula (5A), $R^{12}$ to $R^{15}$ each independently represent a hydrogen atom, or a hydrocarbon group having from 1 to 20 carbon atoms, and they may be the same or different. For the hydrocarbon group having from 1 to 20 carbon atoms, referred to are the same as those mentioned hereinabove. Preferably, in formula (5A), $R^{12}$ and $R^{15}$ each are independently a hydrocarbon group having from 1 to 20 carbon atoms; and $R^{13}$ and $R^{14}$ are both hydrogen atoms. The transition metal compound of the preferred type ensures higher activity. Also preferred is the group of formula (5A) where $R^{12}$ to $R^{15}$ are all methyl groups, as the transition metal compound of that type also ensures higher activity.

In case where V in formula (4) is represented by the following general formula (5B):

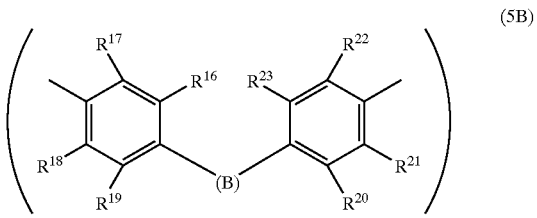

(5B)

M, X, n, $R^1$ to $R^5$ and $R^6$ in that formula (4) may have the same meanings as those mentioned hereinabove. More preferably, however, X in formula (4) is a monovalent anion, even more preferably selected from a halogen atom and an alkyl group. For the hydrocarbon group having from 1 to 20 carbon atoms for $R^{16}$, $R^{17}$, $R^{19}$, $R^{20}$, $R^{22}$ and $R^{23}$ in formula (5B), referred to are the same as those mentioned hereinabove. Preferably, in formula (5B), $R^{16}$, $R^{17}$, $R^{19}$, $R^{20}$, $R^{22}$ and $R^{23}$ are all hydrogen atoms, and $R^{18}$ and $R^{21}$ each are a methyl or ethyl group. The transition metal compound of the preferred type gives a catalyst for α-olefin production, and the catalyst ensures higher activity while retarding the formation of heavy matters and waxy matters.

B represents —(R²⁴₂C)ₘ—, —R²⁴₂Si—, —O—, —S—, or —R²⁴N—; and R²⁴ represents a hydrogen atom, or a hydrocarbon group having from 1 to 20 carbon atoms. For the hydrocarbon group having from 1 to 20 carbon atoms, referred to are those mentioned hereinabove. m is an integer falling between 0 and 4. $R^{16}$ and $R^{23}$ may be bonded to each other to form a ring. In case where m is 0, and $R^{16}$ and $R^{23}$ are bonded to each other via a methylene group therebetween, the formula (5B) forms a fluorenyl ring. V in formula (4) is preferably such a fluorenyl group or a sustituted fluorenyl group, as the α-olefin production catalyst containing the transition metal compound of the type retards the formation of side products, heavy matters and waxy matters.

Specific examples of the transition metal compound of formula (1) are mentioned below. b-

[COMPOUND 1]
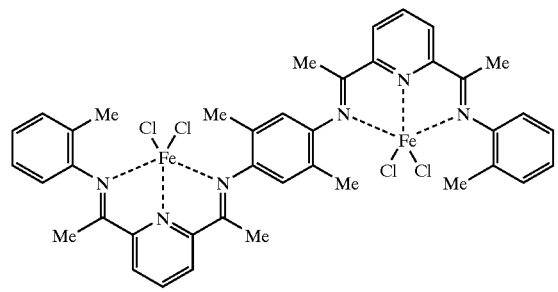
[COMPOUND 2]
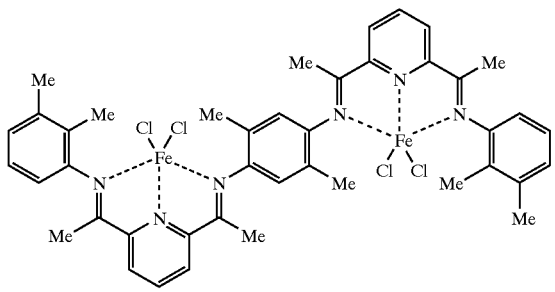
[COMPOUND 3]
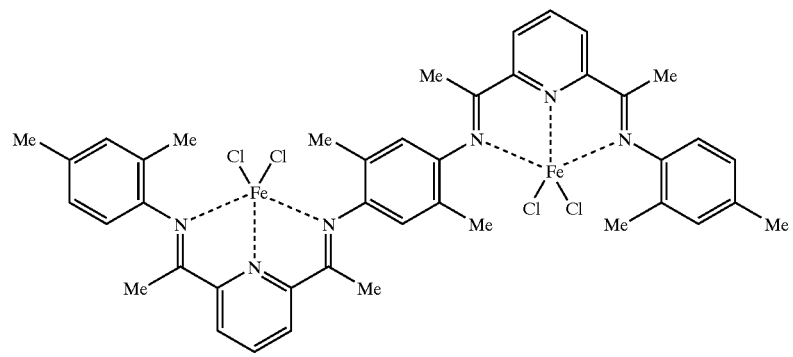
[COMPOUND 4]
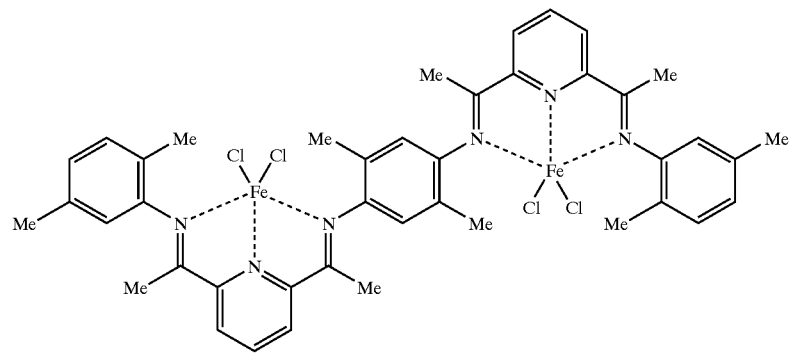
[COMPOUND 5]
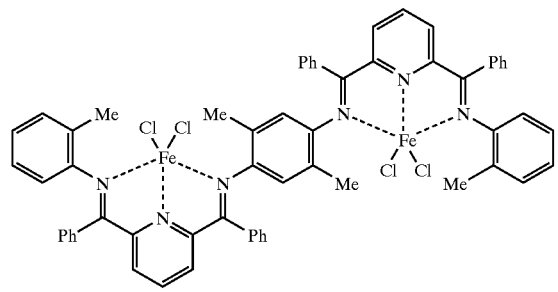
[COMPOUND 6]
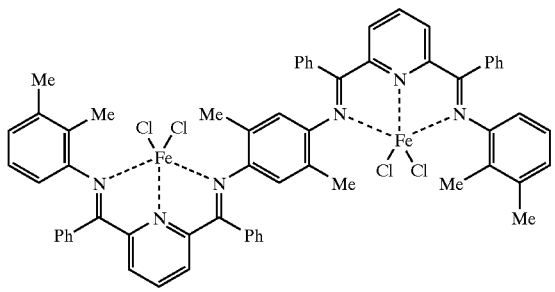

-continued
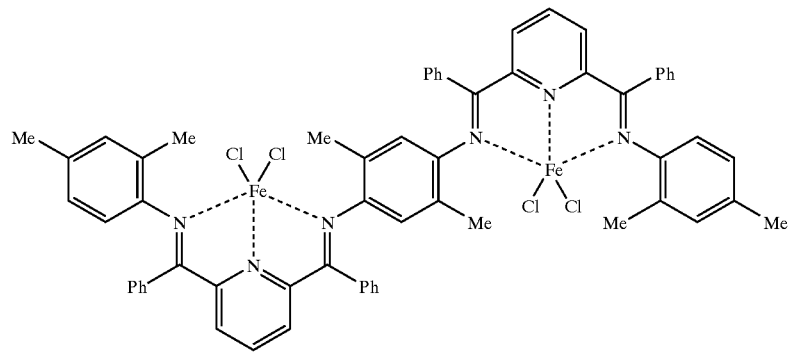
[COMPOUND 7]
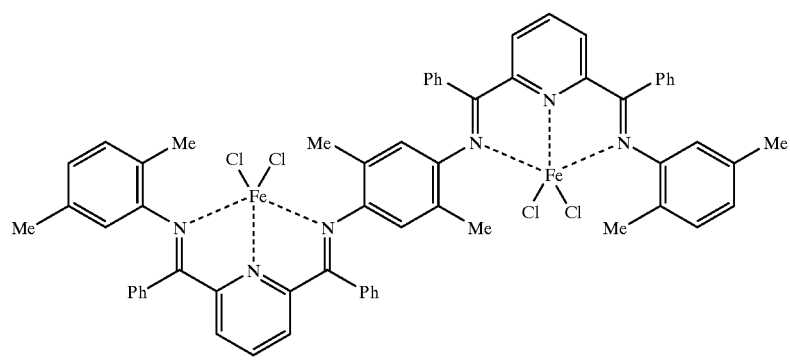
[COMPOUND 8]
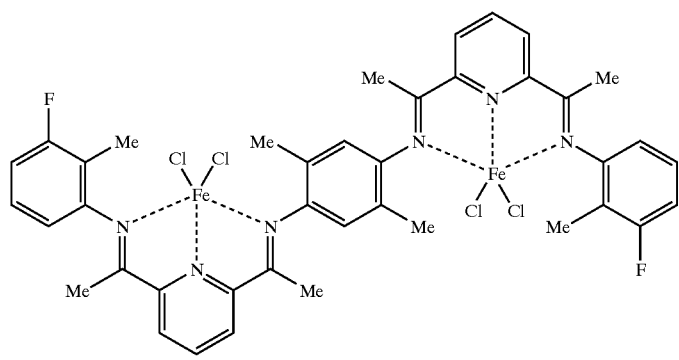
[COMPOUND 9]
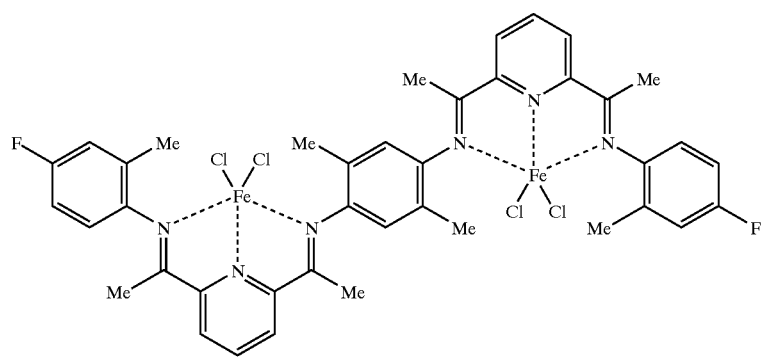
[COMPOUND 10]

[COMPOUND 11]
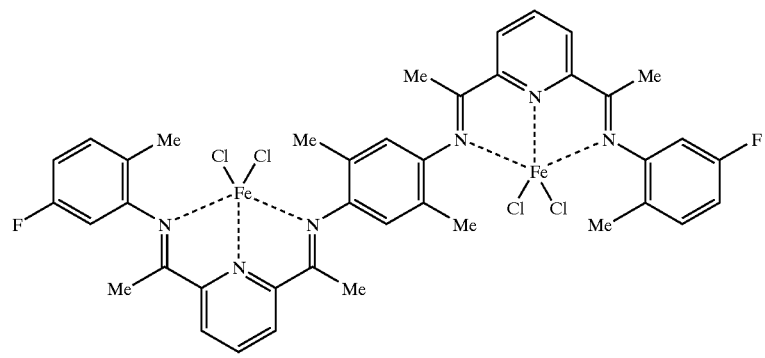
[COMPOUND 12]
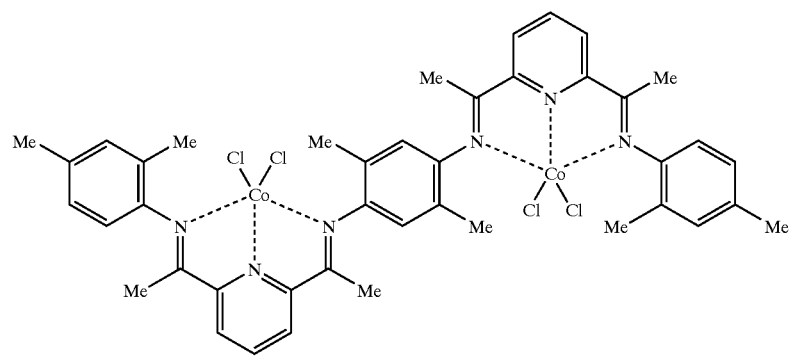
[COMPOUND 13]
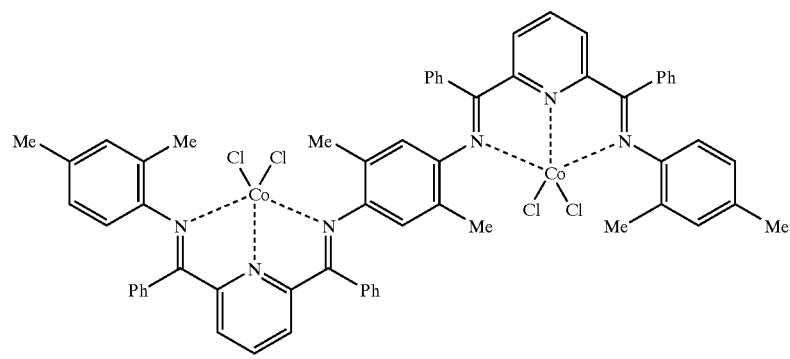
[COMPOUND 14]
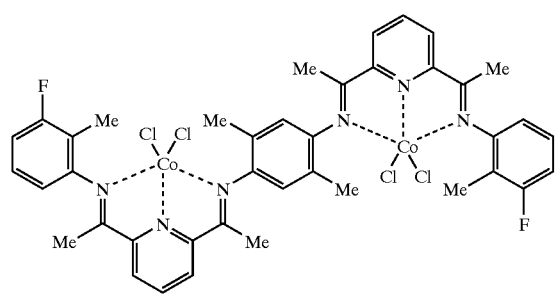
[COMPOUND 15]
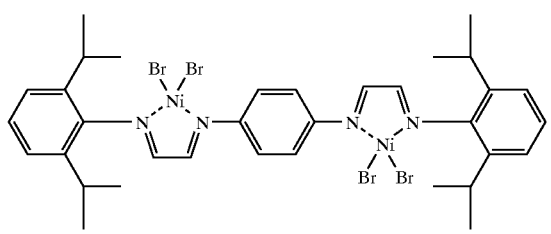

-continued
[COMPOUND 16]
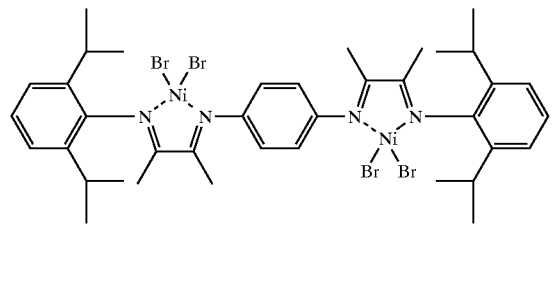
[COMPOUND 17]
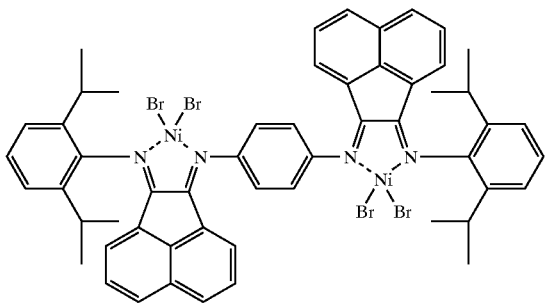
[COMPOUND 18]
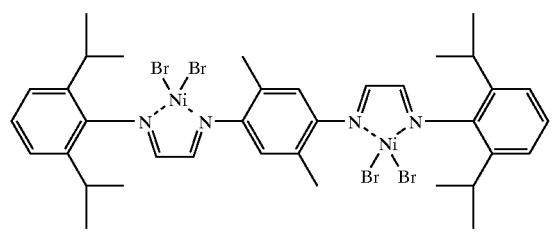
[COMPOUND 19]
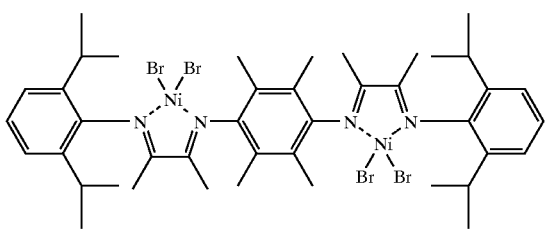
[COMPOUND 20]
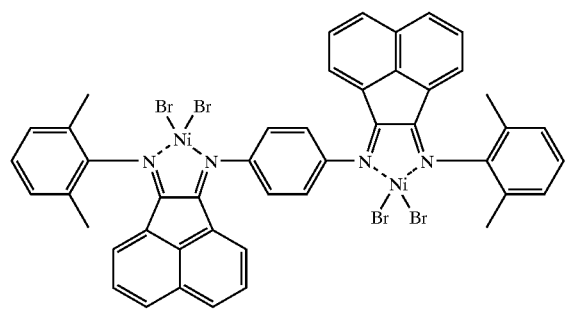
[COMPOUND 21]
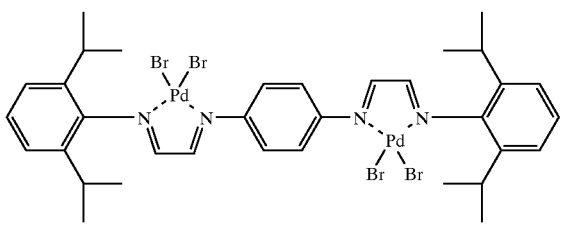
[COMPOUND 22]
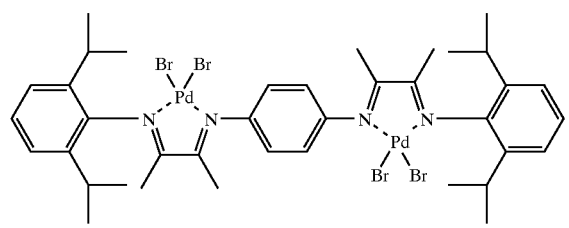
[COMPOUND 23]
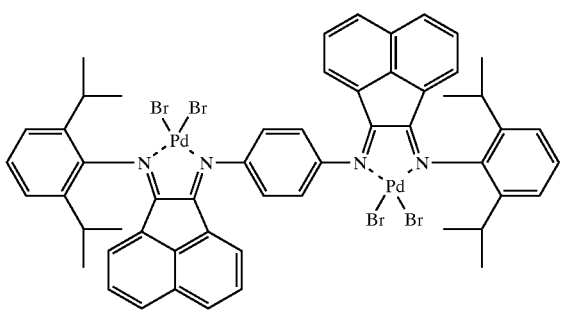
[COMPOUND 24]
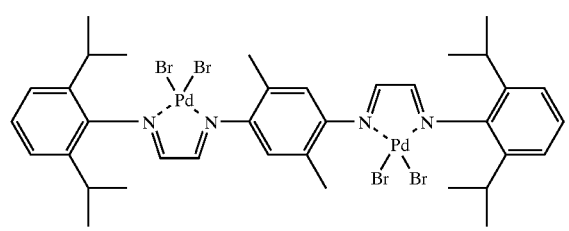
[COMPOUND 25]
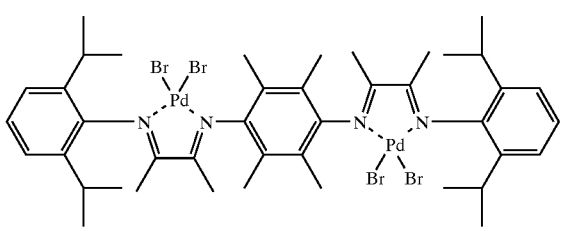

-continued
[COMPOUND 26]
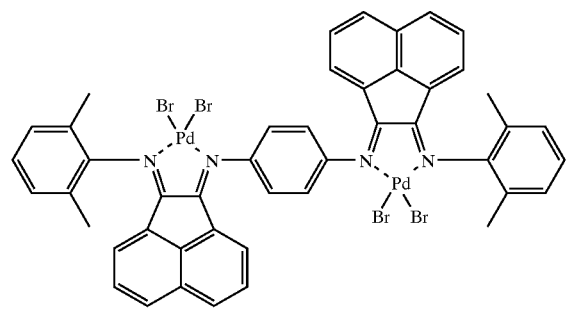
[COMPOUND 27]
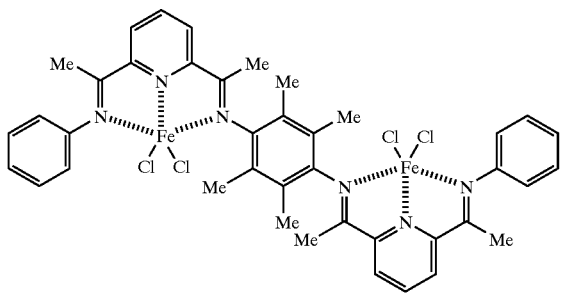
[COMPOUND 28]
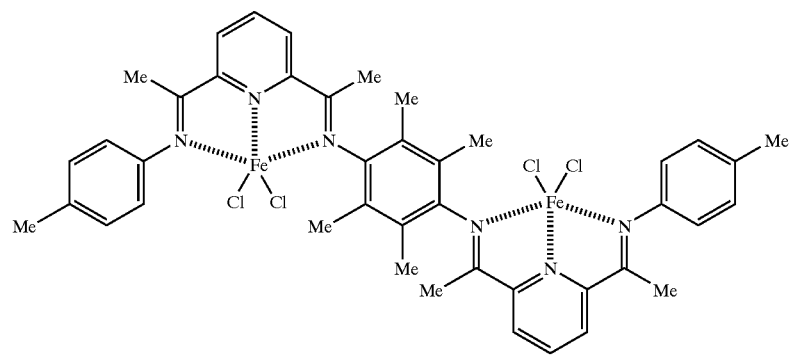
[COMPOUND 29]
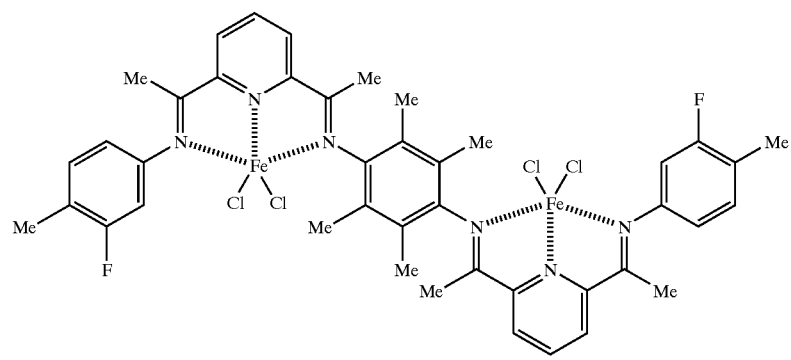
[COMPOUND 30]
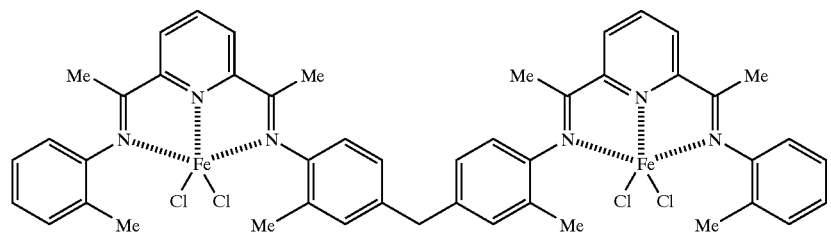
[COMPOUND 31]
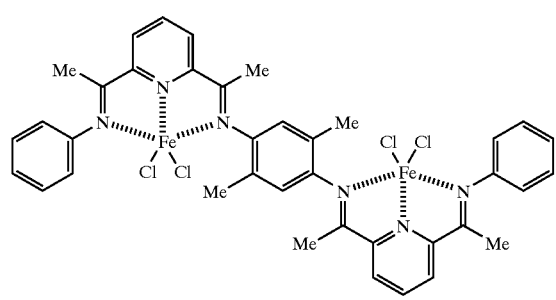
[COMPOUND 32]
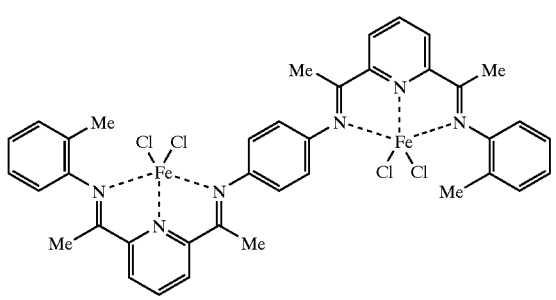

[COMPOUND 33]
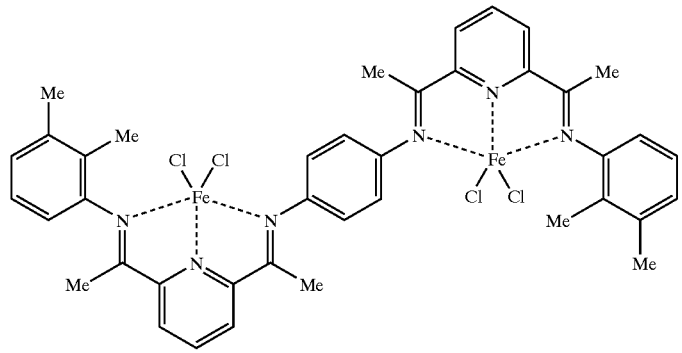
[COMPOUND 34]
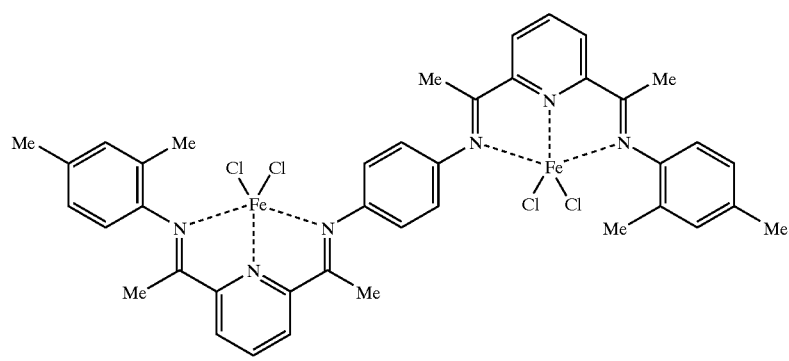
[COMPOUND 35]
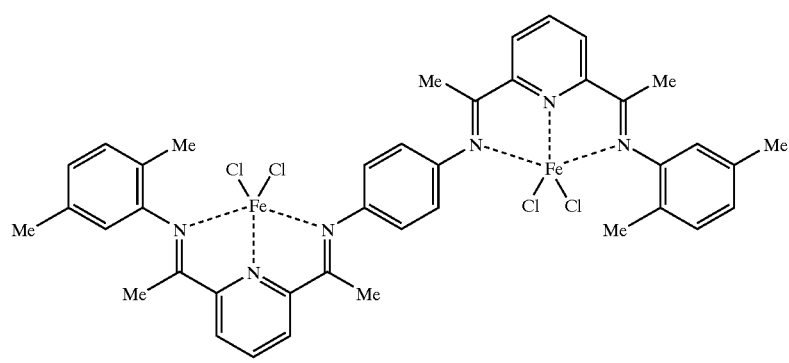
[COMPOUND 36]
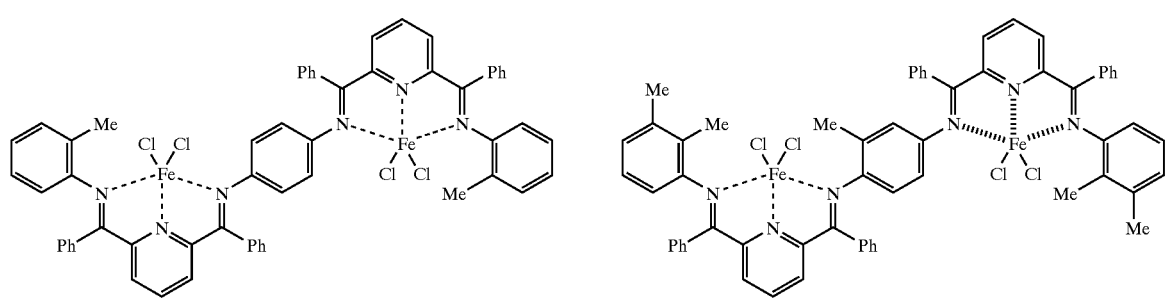

-continued
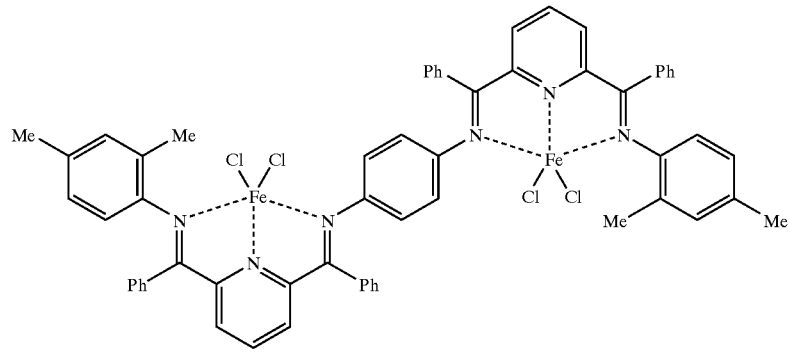
[COMPOUND 38]
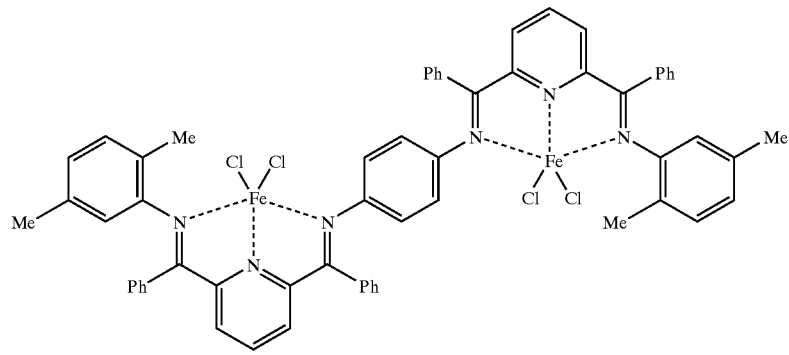
[COMPOUND 39]
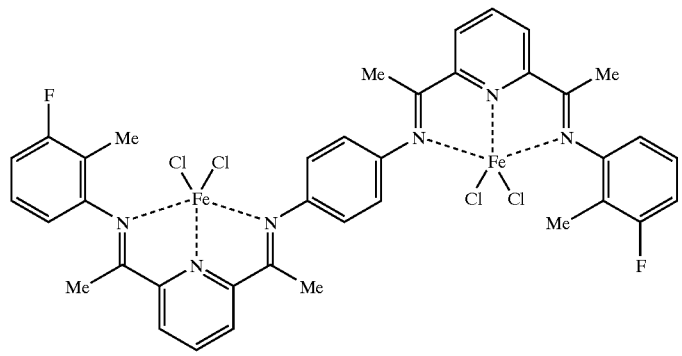
[COMPOUND 40]
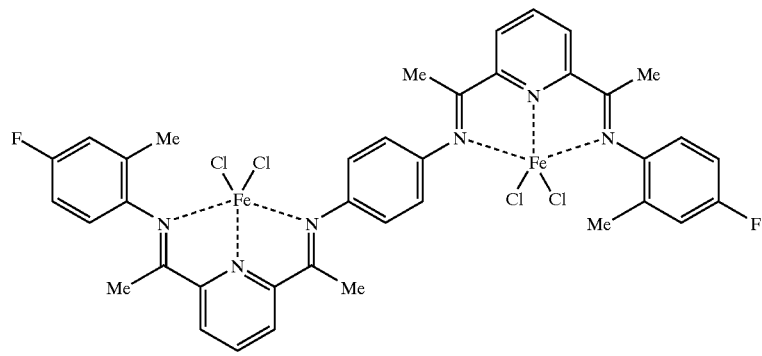
[COMPOUND 41]

-continued
[COMPOUND 42]
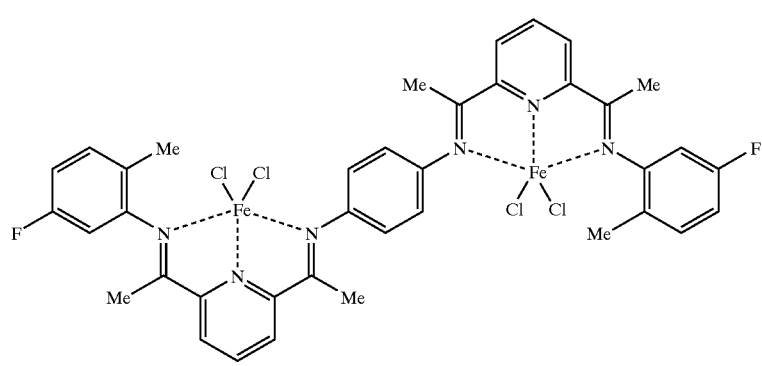
[COMPOUND 43]
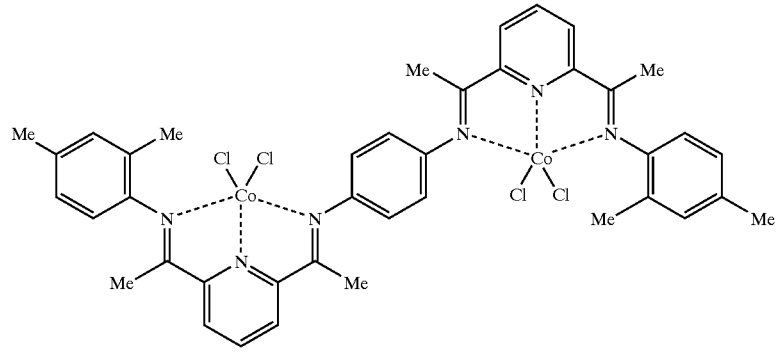
[COMPOUND 44]
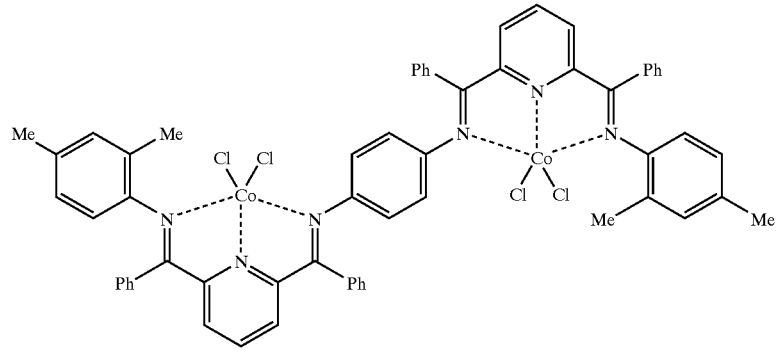
[COMPOUND 45]
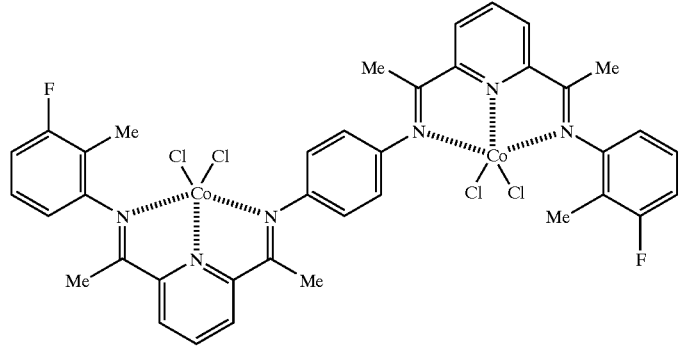
[COMPOUND 46]
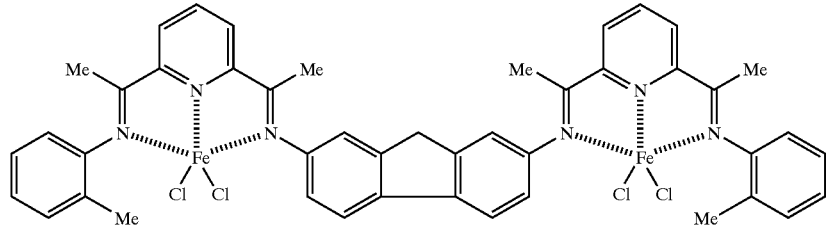

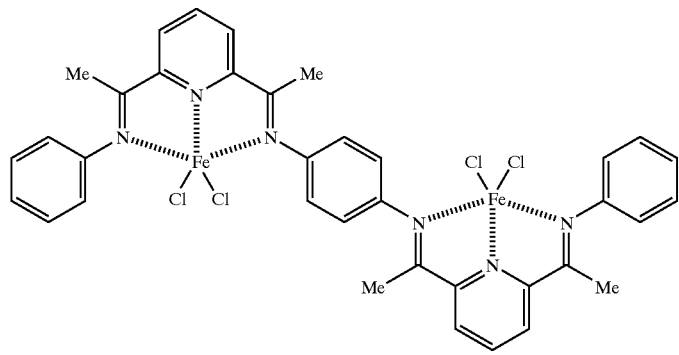

[COMPOUND 47]

Of these, preferred are the iron complexes and the cobalt complexes, as so mentioned hereinabove, but more preferred are the iron complexes. Also preferably, the transition metal compound is represented by the above-mentioned general formula (4), in which $R^6$ is more preferably a phenyl group, or an alkylaryl group substituted by a lower alkyl group such as a methyl or ethyl group.

The transition metal compound of the preferred type may be illustrated as follows:

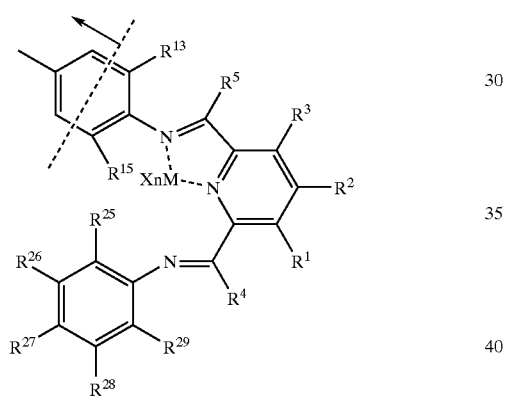

The above illustration is to show the right-side half of the formula (4). In this, $R^{13}$ may be $R^{22}$ as in (5B); and $R^{15}$ may be $R^{21}$ as in (5B). In the compounds illustrated, the groups $R^{13}$, $R^{15}$, $R^{25}$ and $R^{29}$ that are adjacent to the transition metal M often have some influences on the catalytic activity of the compounds. Specifically, the compounds where two of $R^{13}$, $R^{15}$, $R^{25}$ and $R^{29}$ are lower alkyl groups and the other two thereof are hydrogen atoms can form catalysts having higher activity. On the other hand, the compounds where one of $R^{13}$, $R^{15}$, $R^{25}$ and $R^{29}$ is a lower alkyl group and the remaining three of them are hydrogen atoms, or where these $R^{13}$, $R^{15}$, $R^{25}$ and $R^{29}$ are all hydrogen atoms can form catalysts favorable for α-olefin production, and the catalysts retard the formation of heavy matters and waxy matters. To that effect, the compounds of the former type are preferred as ensuring higher α-olefin selectivity. Concretely, the transition compounds, Compound 3, Compound 27, Compound 28 and Compound 29 are preferred, as they can form catalysts having higher activity. For catalysts capable of retarding the formation of heavy matters and waxy matters, preferred are the transition metal compounds, Compound 31, Compound 34, Compound 46 and Compound 47. For catalysts having higher activity and capable of retarding the formation of heavy matters and waxy matters, preferred is the transition metal compound, Compound 30.

The method for producing the transition metal compounds of formula (1) of the invention is not specifically defined. One example for producing the transition metal compounds having a diimine ligand is described. For producing the transition metal compounds of the invention having a ligand, diimino group, a ketone compound of the following general formula (6) and an aniline compound of the following general formula (7) are reacted along with a phenylenediamine compound of the following general formula (8A) or a compound of the following general formula (8B). In formula (7), $R^{25}$ to $R^{29}$ each independently represent a hydrogen atom, a methyl group, an ethyl group or the like.

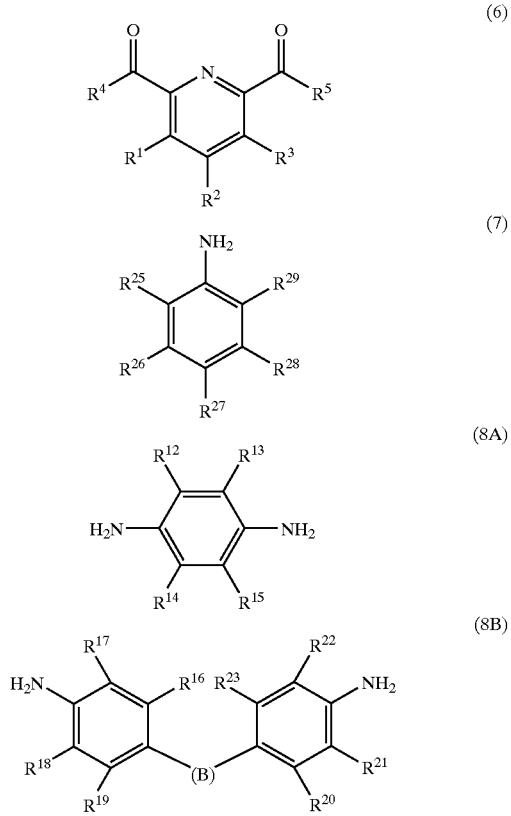

In reacting these compounds, an organic acid such as forming acid or the like may be used as a catalyst. The ligand thus prepared is then reacted with a halide of a transition metal M ($MX^1n$, where $X^1$ indicates a halogen atom) or its hydrate to give the transition metal compound of formula (1).

2. Olefin Polymerization Catalyst

One type of the olefin polymerization catalyst of the invention comprises the following components (A) and (B): (A) a transition metal compound that contains a transition metal of Groups 8 to 10 of the Periodic Table, at least two, hetero atom-containing hydrocarbon groups, and a crosslinking group; and (B) at least one compound selected from a compound group of (B-1) organoaluminium compounds, (B-2) ionic compounds capable of being converted into cationic transition metal compounds through reaction with the transition metal compound, (B-3) Lewis acids, and (B-4) clay, clay minerals and ion-exchanging layered compounds.

Another type of the olefin polymerization catalyst of the invention comprises the following components (A), (B) and (C): (A) a transition metal compound that contains a transition metal of Groups 8 to 10 of the Periodic Table, at least two, hetero atom-containing hydrocarbon groups, and a crosslinking group; (B) at least one compound selected from a compound group of (B-1) organoaluminium compounds, (B-2) ionic compounds capable of being converted into cationic transition metal compounds through reaction with the transition metal compound, (B-3) Lewis acids, and (B-4) clay, clay minerals and ion-exchanging layered compounds; and (C) an organometallic compound.

The constituent components are described below.

Component (A)

The component (A) is a transition metal compound that contains a transition metal of Groups 8 to 10 of the Periodic Table, at least two, hetero atom-containing hydrocarbon groups, and a crosslinking group. The transition metal of Groups 8 to 10 of the Periodic Table is not specifically defined, preferably including iron, cobalt, palladium and nickel. The hetero atom-containing hydrocarbon group includes, for example, an oxygen-containing hydrocarbon group (e.g., alkoxy group, etc.), a nitrogen-containing hydrocarbon group (e.g., amino group, imino group, etc.), a silicon-containing hydrocarbon group (e.g., silyl group represented by —SiR$_3$, etc.). Of these, preferred is a nitrogen-containing hydrocarbon group. The crosslinking group is not specifically defined, including, for example, a hetero atom-containing group and a hydrocarbon group. Of these, preferred is a hydrocarbon group, and more preferred is an aromatic group-containing crosslinking group. More concretely, the component (A) includes the transition metal compounds mentioned hereinabove. The component (A) may be a single transition metal compound of formula (1) mentioned above, or may also be a mixture of two or more such transition metal compounds that differ in the degree of polymerization, Z.

Component (B)

The component (B) is at least one selected from the compound group of (B-1) organoaluminium compounds, (B-2) ionic compounds capable of being converted into cationic transition metal compounds through reaction with the transition metal compound, (B-3) Lewis acids, and (B-4) clay, clay minerals and ion-exchanging layered compounds.

(B-1) Organoaluminium Compound

The organoaluminium compound for use herein includes alkyl group-containing aluminium compounds of the following general formula (9):

wherein $R^{30}$ represents an alkyl group having from 1 to 8, preferably from 1 to 4 carbon atoms, and a plurality of $R^{30}$'s, if any, may be the same or different; $X^2$ represents a hydrogen atom or a halogen atom; $0 < m \leq 3$, but preferably m is 2 or 3, most preferably 3; $0 \leq n < 3$, but preferably m is 0 or 1; and $0 < m+n \leq 3$.

The organoaluminium compound further includes linear aluminoxanes of the following general formula (10):

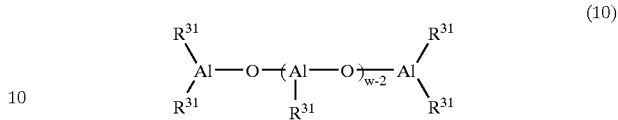

wherein $R^{31}$ represents a hydrocarbon group, such as an alkyl, alkenyl, aryl or arylalkyl group having from 1 to 20, preferably from 1 to 12 carbon atoms, or a halogen atom; w indicates a mean degree of polymerization of the compound, and is an integer generally falling between 2 and 50, preferably between 2 and 40; and $R^{31}$'s may be the same or different, and cyclic aluminoxanes of the following general formula (11)

wherein $R^{31}$ and w have the same meanings as in formula (10)

For producing the aluminoxanes, an alkylaluminium may be contacted with a condensing agent such as water or the like. The method is not specifically defined, and may be effected in any ordinary manner. For this, for example, <1> an organoaluminium compound is dissolved in an organic solvent and then contacted with water; <2> an organoaluminium compound is made present in the polymerization system, and water is added to the polymer formed; <3> crystal water existing in metal salts and the like, or water having adsorbed to inorganic or organic matters is applied to and reacted with an organoaluminium compound; <4> a tetraalkyldialuminoxane is reacted with a trialkylaluminium, and then with water.

The aluminoxanes may be soluble or insoluble in hydrocarbon solvents. Preferably, however, they are soluble in hydrocarbon solvents, and have a residual organoaluminium compound content of at most 10% by weight measured through $^1$H-NMR. More preferably, they have a residual organoaluminium compound content of from 3 to 5% by weight or smaller, even more preferably from 2 to 4% by weight or smaller. It the residual organoaluminium compound content thereof is larger than 10% by weight, the aluminoxane will lower the polymerization activity of the catalyst comprising.

To obtain the preferred aluminoxanes, for example, employable is a so-called dry-up method that comprises dissolving an ordinary aluminoxane in a solvent, followed by drying up the resulting aluminoxane solution under heat under reduced pressure to remove the solvent.

For removing the matters insoluble in hydrocarbon solvents from aluminoxanes, for example, the insoluble matters are spontaneously precipitated in an aluminoxane solution in a hydrocarbon solvent and then removed from the solution through decantation. Alternatively, the insoluble matters may also be removed through centrifugation or the like. With that, the solubilized component thus recovered is filtered through a G5 glass filter or the like in a nitrogen atmosphere. The method is preferable as it ensures complete removal of the insoluble matters. The aluminoxanes thus prepared will often gel when stored for long. Therefore, it is desirable that they are used in the invention within 48 hours after their preparation. More preferably, they are used immediately after their preparation. The proportion of the aluminoxane to the hydrocarbon solvent in which it is processed is not specifically defined, but it is desirable that the aluminoxane concentration in the hydrocarbon solvent falls between 0.5 and 10 mols, in terms of the aluminium atom, in one liter of the hydrocarbon solvent.

The hydrocarbon solvent includes, for example, aromatic hydrocarbons such as benzene, toluene, xylene, cumene, cymene, etc.; aliphatic hydrocarbons such as pentane, hexane, heptane, octane, decane, dodecane, hexadecane, octadecane, etc.; alicyclic hydrocarbons such as cyclopentane, cyclohexane, cyclooctane, methylcyclopentane, etc.; petroleum fractions such as naphtha, kerosene, light gas oil, etc.

For the aluminoxane for use herein, preferred are alkylaluminoxanes such as methylaluminoxane, ethylaluminoxane, isobutylaluminoxane, etc. Of these, more preferred is methylaluminoxane. One or more of these aluminoxanes may be used either singly or as combined, and aluminoxanes having different alkyl groups (e.g., methyl group and isobutyl group) are also usable herein.

(B-2) Ionic Compound:

Any ionic compound capable of being converted into cationic transition metal compounds through reaction with the transition metal compound is employable herein. Especially preferred for use herein are compounds of the following general formulae (12) and (13), as being able to efficiently form polymerization-active points.

  (12)

  (13)

wherein $L^2$ represents $M^1$, $R^{33}R^{34}M^2$, $R^{35}{}_3C$ or $R^{36}M^2$;

$L^1$ represents a Lewis base;

$[Z]^-$ represents a non-coordinating anion $[Z^1]^-$ or $[Z^2]^-$;

$[Z^1]^-$ represents an anion of a plurality of groups bonded to an element, $[M^3G^1G^2 \ldots G^f]^-$;

$M^3$ represents an element of Groups 5 to 15 of the Periodic Table, preferably an element of Groups 13 to 15 of the Periodic Table; $G^1$ to $G^f$ each represents a hydrogen atom, a halogen atom, an alkyl group having from 1 to 20 carbon atoms, a dialkylamino group having from 2 to 40 carbon atoms, an alkoxy group having from 1 to 20 carbon atoms, an aryl group having from 6 to 20 carbon atoms, an aryloxy group having from 6 to 20 carbon atoms, an alkylaryl group having from 7 to 40 carbon atoms, an arylalkyl group having from 7 to 40 carbon atoms, a halogen-substituted hydrocarbon group having from 1 to 20 carbon atoms, an acyloxy group having from 1 to 20 carbon atoms, an organometalloid group, or a hetero atom-containing hydrocarbon group having from 2 to 20 carbon atoms; and at least two of $G^1$ to $G^f$ may form a ring;

f is an integer, indicating [(atomic valency of the center metal $M^3$)+1];

$[Z^2]^-$ represents a conjugated base of a single Brønsted acid of which the logarithm of the reciprocal of the acid dissociation constant (pKa) is at most −10, or of a combination of such a Brønsted acid and a Lewis acid, or represents a conjugated base of an ordinary ultrastrong acid, and optionally, this may be coordinated with a Lewis base;

$R^{32}$ represents a hydrogen atom, an alkyl group having from 1 to 20 carbon atoms, an aryl group having from 6 to 20 carbon atoms, an alkylaryl group, or an arylalkyl group;

$R^{33}$ and $R^{34}$ each represent a cyclopentadienyl group, a substituted cyclopentadienyl group, an indenyl group, or a fluorenyl group;

$R^{35}$ represents an alkyl group having from 1 to 20 carbon atoms, an aryl group, an alkylaryl group, or an arylalkyl group;

$R^{36}$ represents a macrocyclic ligand such as tetraphenylporphyrin, phthalocyanine or the like;

h is an integer of from 1 to 3, indicating the ionic valency of $[L^1—R^{32}]$ or $[L^2]$;

a is an integer of at least 1;

b=(h×a);

$M^1$ represents an element of Groups 1 to 3, 11 to 13 and 17 of the Periodic Table; and $M^2$ represents an element of Groups 7 to 12 of the Periodic Table.

Specific examples of $L^1$ are amines such as ammonia, methylamine, aniline, dimethylamine, diethylamine, N-methylaniline, diphenylamine, N,N-dimethylaniline, trimethylamine, triethylamine, tri-n-butylamine, methyldiphenylamine, pyridine, p-bromo-N,N-dimethylaniline, p-nitro-N,N-dimethylaniline, etc.; phosphines such as triethylphosphine, triphenylphosphine, diphenylphosphine, etc.; thioethers such as tetrahydrothiophene, etc.; esters such as ethyl benzoate, etc.; nitriles such as acetonitrile, benzonitrile, etc.

Specific examples of $R^{32}$ are a hydrogen atom, a methyl group, an ethyl group, a benzyl group, a trityl group, etc. Specific examples of $R^{33}$ and $R^{34}$ are a cyclopentadienyl group, a methylcyclopentadienyl group, an ethylcyclopentadienyl group, a pentamethylcyclopentadienyl group, etc. Specific examples of $R^{35}$ are a phenyl group, a p-tolyl group, a p-methoxyphenyl group, etc. Specific examples of $R^{36}$ are tetraphenylporphine, phthalocyanine, methallyl, etc. Specific examples of $M^1$ are Li, Na, K, Ag, Cu, Br, I, etc. Specific examples of $M^2$ are Mn, Fe, Co, Ni, Zn, etc.

In $[Z^1]^-$ indicating $[M^3G^1G^2 \ldots G^f]^-$, $M^3$ includes B, Al, Si, P, As, Sb, etc., but is preferably B or Al. Specific examples of the dialkylamino group for $G^1$, $G^2$ to $G^f$ are a dimethylamino group, a diethylamino group, etc.; those of the alkoxy group and the aryloxy group are a methoxy group, an ethoxy group, an n-butoxy group, a phenoxy group, etc.; those of the hydrocarbon group are a methyl group, an ethyl group, an n-propyl group, an isopropyl group, an n-butyl group, an isobutyl group, an n-octyl group, an n-eicosyl group, a phenyl group, a p-tolyl group, a benzyl group, a 4-t-butylphenyl group, a 3,5-dimethylphenyl group, etc.; those of the halogen atom are fluorine, chlorine, bromine and iodine atoms; those of the hetero atom-containing hydrocarbon group are a p-fluorophenyl group, a 3,5-difluorophenyl group, a pentafluoropoheniyl group, a 3,4,5-trifluorophenyl group, a 3,5-bis(trifluoromethyl)phenyl group, a bis(trimethylsilyl)methyl group, etc.; those of the organometalloid group are a pentamethylantimonyl group, a trimethylsilyl group, a trimethylgermyl group, a diphenylarsenyl group, a dicyclohexylantimonyl group, a diphenylboryl group, etc.

Specific examples of the non-coordinating anion, $[Z^2]^-$ that indicates a conjugated base of a single Brønsted acid having pKa of at most −10, or of a combination of such a Brønsted acid and a Lewis acid are a trifluoromethanesulfonate anion $(CF_3SO_3)^-$, a bis(trifluoromethanesulfonyl)

methyl anion, a bis(trifluoromethanesulfonyl)benzyl anion, a bis(trifluoromethanesulfonyl)amido anion, a perchlorate anion $(ClO_4)^-$, a trifluoroacetate anion $(CF_3CO_2)^-$, a hexafluoroantimonyl anion $(SbF_6)^-$, a fluorosulfonate anion $(FSO_3)^-$, a chlorosulfonate anion $(ClSO_3)^-$, a fluorosulfonate/hexafluoroantimonyl anion $(FSO_3/SbF_5)^-$, a fluorosulfonate/hexafluoroarsenyl anion $(FSO_3/AsF_5)^-$, a trifluoromethanesulfonate/hexafluoroantimonyl anion $(CF_3SO_3/SbF_5)^-$, etc.

Specific examples of the compounds for the component (B-2) are triethylammonium tetraphenylborate, tri-n-butylammonium tetraphenylborate, trimethylammonium tetraphenylborate, tetraethylammonium tetraphenylborate, methyl(tri-n-butyl)ammonium tetraphenylborate, benzyl(tri-n-butyl)ammonium tetraphenylborate, dimethyldiphenylammonium tetraphenylborate, triphenyl(methyl) ammonium tetraphenylborate, trimethylanilinium tetraphenylborate, methylpyridinium tetraphenylborate, benzylpyridinium tetraphenylborate, methyl(2-cyanopyridinium)tetraphenylborate, triethylammonium tetrakis(pentafluorophenyl)borate, tri-n-butylammonium tetrakis(pentafluorophenyl)borate, triphenylammonium tetrakis(pentafluorophenyl)borate, tetra-n-butylammonium tetrakis(pentafluorophenyl)borate, tetraethylammonium tetrakis(pentafluorophenyl)borate, benzyl(tri-n-butyl) ammonium tetrakis(pentafluorophenyl)borate, methyldiphenylammonium tetrakis(pentafluorophenyl)borate, triphenyl (methyl)ammonium tetrakis(pentafluorophenyl)borate, methylanilinium tetrakis(pentafluorophenyl)borate, dimethylanilinium tetrakis(pentafluorophenyl)borate, trimethylanilinium tetrakis(pentafluorophenyl)borate, methylpyridinium tetrakis(pentafluorophenyl)borate, benzylpyridinium tetrakis(pentafluorophenyl)borate, methyl(2-cyanopyridinium)tetrakis(pentafluorophenyl)borate, benzyl(2-cyanopyridinium)tetrakis(pentafluorophenyl)borate, methyl(4-cyanopyridinium)tetrakis(pentafluorophenyl) borate, triphenylphosphonium tetrakis(pentafluorophenyl) borate, dimethylanilinium tetrakis[bis(3,5-ditrifluoromethyl)phenyl]borate, ferrocenium tetraphenylborate, silver tetraphenylborate, trityl tetraphenylborate, tetraphenylporphyrylmanganese tetraphenylborate, ferrocenium tetrakis(pentafluorophenyl) borate, (1,1'-dimethylferrocenium)tetrakis (pentafluorophenyl)borate, decamethylferrocenium tetrakis (pentafluorophenyl)borate, silver tetrakis (pentafluorophenyl)borate, trityl tetrakis(pentafluorophenyl) borate, lithium tetrakis(pentafluorophenyl)borate, sodium tetrakis(pentafluorophenyl)borate, tetraphenylporphyrylmanganese tetrakis(pentafluorophenyl)borate, silver tetrafluoroborate, silver hexafluorophosphate, silver hexafluoroarsenate, silver perchlorate, silver trifluoroacetate, silver trifluoromethanesulfonate, etc. For the component (B-2), especially preferred are boron compounds.

(B-3) Lewis Acid

Lewis acids for the component (B-3) are not specifically defined, and may be organic compounds and solid inorganic compounds. Preferred organic compounds are boron compounds and aluminium compounds, and preferred inorganic compounds are magnesium compounds and aluminium compounds, as they can effectively form active points. The aluminium compounds include, for example, bis(2,6-di-t-butyl-4-methylphenoxy)methylaluminium, (1,1'-bis-2-naphthoxy)methylaluminium, etc.; the magnesium compounds include, for example, magnesium chloride, diethoxymagnesium, etc.; the aluminium compounds include, for example, aluminium oxide, aluminium chloride, etc.; the boron compounds include, for example, triphenylboron, tris(pentafluorophenyl)boron, tris[3,5-bis (trifluoromethyl)phenyl]boron, tris[(4-fluoromethyl)phenyl] boron, trimethylboron, triethylboron, tri-n-butylboron, tris (fluoromethyl)boron, tris(pentafluoroethyl)boron, tris (nonafluorobutyl)boron, tris(2,4,6-trifluorophenyl)boron, tris(3,5-difluorophenyl)boron, tris[3,5-bis(trifluoromethyl) phenyl]boron, bis(pentafluorophenyl)fluoroboron, diphenylfluoroboron, bis(pentafluorophenyl)chloroboron, dimethylfluoroboron, diethylfluoroboron, di-n-butylfluoroboron, pentafluorophenyldifluoroboron, phenyldifluoroboron, pentafluorophenyldichloroboron, methyldifluoroboron, ethyldifluoroboron, n-butyldifluoroboron, etc. One or more of these Lewis acids may be used herein either singly or as combined.

(B-4) Clay, Clay Mineral and Ion-exchanging Layered Compound

Clay is an aggregate of fine hydrous silicate minerals. It is plastic when kneaded with a suitable amount of water, and is rigid when dried. When baked at high temperatures, it is sintered. Clay minerals are hydrous silicates which are the essential components constituting clay. In preparing the olefin polymerization catalyst, usable is any of such clay and clay minerals, and these may be natural ones or synthetic products.

Ion-exchanging layered compounds for the catalyst are characterized by the crystal structure of such that a plurality of crystal planes are laminated in parallel with each other via weak ion-bonding therebetween, in which the ions are exchangeable. Some clay minerals are such ion-exchanging layered compounds.

Specific examples of the component (B-4) are mentioned. For example, phyllosilicic acid compounds belong to clay minerals. Phyllosilicic acid compounds include phyllosilicic acid and phyllosilicates. As natural phyllosilicates, known are montmorillonite, saponite and hectorite of the smectite family; illite and sericite of the mica family; and mixed layer minerals of smectites and micas, or those of micas and vermiculites. As synthetic products, known are fluorotetrasilicon mica, laponite, smectone, etc. Also mentioned are ion-exchanging crystalline compounds having a layered crystal structure, such as $\alpha$-$Zr(HPO_4)_2$, $\gamma$-$Zr(HPO_4)_2$, $\alpha$-Ti $(HPO_4)_2$, $\gamma$-$Ti(HPO_4)_2$, etc. These are not clay minerals.

Examples of clay and clay minerals which do not belong to ion-exchanging layered compounds include clay having a low montmorillonite content and referred to as bentonite; kibushi clay containing montmorillonite and many other components; gairome clay; sepiolite and palygorskite having a fibrous morphology; and amorphous or low-crystalline allophane, imogolite, etc. Of these mentioned herein, preferred for the component (B-4) are clay and clay minerals. Concretely, phyllosilicic acid compounds are preferred; smectite is more preferred; and montmorillonite is even more preferred.

Preferably, clay, clay minerals and ion-exchanging layered compounds for the component (B-4) have a volume-average particle size of at most 10 $\mu$m, more preferably at most 3.0 $\mu$m. As a rule, particles have a particle size distribution. For their particle size distribution, preferably, clay, clay minerals and ion-exchanging layered compounds for the component (B-4) have a volume-average particle size of at most 10 $\mu$m and the particles thereof having a volume-average particle size of at most 3.0 $\mu$m account for at least 10% by weight of the component (B-4). More preferably, the compounds for the component (B-4) have a volume-average particle size of at most 10 $\mu$m and the particles thereof having a volume-average particle size of at most 1.5 $\mu$m account for at least 10% by weight of the component (B-4). For measuring the volume-average particle size and the particle size distribution of the compounds for the component (B-4), for example, used is an apparatus for measuring the size of particles from the layer ray transmittance through the particles (for example, GALAI Production's CIS-1).

For the component (B-4), it is desirable that clay, clay minerals and ion-exchanging layered compounds are chemically treated for the purpose of removing impurities from them or for modifying their structures and functions to those more preferred for catalytic ingredients.

For example, the compounds may be processed with an organosilane compound. The organosilane compound includes those of the following general formula (14):

$$R^{37}{}_n SiX^3{}_{4-n} \qquad (14)$$

wherein $R^{37}$ represents a substituent in which the atom directly bonding to the silicon atom is a carbon, silicon or hydrogen atom; $X^3$ represents a substituent in which the atom directly bonding to the silicon atom is a halogen, oxygen or nitrogen atom; a plurality of $R^{37}$'s and $X^3$'s, if any, may be the same or different; n indicates an integer of from 1 to 3.

The organosilane compound further includes bis-silyl compounds of the following general formula (15):

$$X^3{}_{4-n} Si(CH_2)_m SiX^3{}_{4-n} \qquad (15)$$

wherein $X^3$ represents a substituent in which the atom directly bonding to the silicon atom is a halogen, oxygen or nitrogen atom, and a plurality of $X^3$'s, if any, may be the same or different; m indicates from 1 to 10; and n indicates from 1 to 3,
and also polycyclic polysiloxanes, polysilazanes, etc.

Specific examples of the organosilane compounds of above formulae are trialkylsilyl chlorides such as trimethylsilyl chloride, triethylsilyl chloride, triisopropylsilyl chloride, t-butyldimethylsilyl chloride, t-butyldiphenylsilyl chloride, phenethyldimethylsilyl chloride, etc.; dialkylsilyl dichlorides, diarylsilyl dichlorides and alkylarylsilyl dichlorides such as dimethylsilyl dichloride, diethylsilyl dichloride, diisopropylsilyl dichloride, di-n-hexylsilyl dichloride, dicyclohexylsilyl dichloride, docosylmethylsilyl dichloride, bis(phenethyl)silyl dichloride, methylphenethylsilyl dichloride, diphenylsilyl dichloride, dimesitylsilyl dichloride, ditolylsilyl dichloride, etc.

Also usable herein are other silyl halides to be derived from the above-mentioned compounds by substituting the chloride moiety therein with any other halogens; disilazanes such as bis(trimethylsilyl)amide, bis(triethylsilyl)amide, bis(triisopropylsilyl)amide, bis(dimethylethylsilyl)amide, bis(diethylmethylsilyl)amide, bis(dimethylphenylsilyl)amide, bis(dimethyltolylsilyl)amide, bis(dimethylmenthylsilyl)amide, etc.; trialkylsilyl hydroxides such as trimethylsilyl hydroxide, triethylsilyl hydroxide, triisopropylsilyl hydroxide, tert-butyldimethylsilyl hydroxide, phenethyldimethylsilyl hydroxide, etc.; polysilanols generally known as peralkylpolysiloxypolyols; bissilyls such as bis(methyldichlorosilyl)methane, 1,2-bis(methyldichlorosilyl)ethane, bis(methyldichlorosilyl)octane, bis(triethoxysilyl)ethane, etc.; silane hydrides such as dimethylchlorosilane, (N,N-dimethylamino)dimethylsilane, duisobutylchlorosilane, etc. One or more of these organosilane compounds may be used herein either singly or as combined.

Of the organosilane compounds, preferred are those having at least one alkyl group directly bonding to the silicon atom. Favorably used are alkylsilyl halides, more favorably dialkylsilyl halides. Treatment with such an organosilane compound is preferably effected in the presence of water to ensure better results. In that case, water breaks the crystal structure (especially the layered crystal structure) of clay and others, thereby enhancing the contact efficiency between the organosilane compound and the thus-broken clay and others. Specifically, water expands the layer-to-layer spaces in the crystal structure of clay and others, thereby promoting the diffusion of an organosilane compound into the layered crystals. The treatment of the compounds for the component (B-4) with such an organosilane compound to prepare organosilane-treated compounds for the component (B-4) is described concretely. First, water is added to the component (B-4) to prepare an aqueous colloidal solution of the component (B-4). Next, an organosilane compound such as that mentioned above is added to the thus-prepared, aqueous colloidal solution of the component (B-4), and stirred under heat, whereby the component (B-4) is processed with the organosilane compound. This treatment may be effected at room temperature to 200° C. Preferably, it is effected at a temperature around 100° C. at which it will be facilitated. The treatment time will vary, depending on the type of the component (B-4) to be treated and on the treatment temperature, but may fall between 0.5 and 24 hours.

The amount of the organosilane compound to be used for treating the component (B-4) may fall between 0.001 and 1000 mols, but preferably between 0.01 and 100 mols, in terms of the silicon atom in the organosilane compound, per kg of the component (B-4).

One or more of the compounds mentioned above may be used either singly or as combined, for the component (B-4).

The proportion of the components (A) and (B) of the polymerization catalyst of the invention is described. In case where the compound (B-1) is used for the component (B), the molar ratio of the two components preferably falls between 1/1 and 1/1000000, more preferably between 1/10 and 1/10000; in case where the compound (B-2) is used, the molar ratio preferably falls between 10/1 and 1/100, more preferably between 2/1 and 1/10; and in case where the compound (B-3) is used, the molar ratio preferably falls between 10/1 and 1/200, more preferably between 5/1 and 1/100, even more preferably between 2/1 and 1/50. In case where the compound (B-4) is used for the component (B), the amount of the component (A) shall fall generally between 0.01 and 100 mmols, but preferably between 0.1 and 1 mmol, relative to the unit weight (g) of the compound (B-4). It is desirable that the compound (B-4) for the component (B) is pre-treated with the organometallic compound (C) to be mentioned hereinunder, especially with an organoaluminium compound. In general, the amount of the component (C) will fall between 0.1 and 1000 mmols, preferably between 1 and 100 mmols, relative to the unit weight (g) of the compound (B-4). However, even though an excessive amount of the component (C) is used for treating the compound (B-4), it may be removed from the system by washing the suspension slurry of clay and others with a solvent.

One or more of the compounds (B-1), (B-2), (B-3) and (B-4) may be used herein either singly or as combined.

(C) Organometallic Compound

The olefin polymerization catalyst of the invention may optionally contain an organometallic compound (C).

For the organometallic compound for the component (C), usable are organozinc compounds and organoaluminium compounds, but preferred are inexpensive and easily-available organoaluminium compounds. Concretely mentioned for the component (C) are trialkylaluminiums such as trimethylaluminium, triethylaluminium, tripropylaluminium, triisobutylaluminium, tri-tert-butylaluminium, etc.; halogen- or alkoxy group-containing alkylaluminiums such as dimethylaluminium chloride, diethylaluminium chloride, dimethylaluminium methoxide, diethylaluminium ethoxide, etc.; alumoxanes such as methylalumoxane, ethylalumoxane, isobutylalumoxane, etc. Of those, especially preferred are trialkylaluminiums.

The ratio by mol of the catalyst component (C) to the catalyst component (A) may fall between 0.1 and 10000, preferably between 1 and 2000, more preferably between 10 and 1000.

The treatment of contacting the components (A), (B) and (C) with each other is preferably effected in an inert gas stream of argon, nitrogen or the like. Also preferably it is effected in a hydrocarbon solvent such as pentane, hexane, heptane, toluene, xylene or the like. Still preferably, the treatment is effected in the absence of water and other active hydrogen-containing compounds such as those having a hydroxyl group, an amino group or the like that are harmful to the catalyst to be prepared from the components. For this, it is desirable that water and other active hydrogen-containing compounds are removed from the reaction system by the use of the component (C). Accordingly, it is desirable that the catalyst of the invention is prepared by contacting the components (A), (B) and (C) with each other. It is not always necessary that the component (C) is present in the system of preparing the catalyst, but, as the case may be, the component (C) may be added to the polymerization system of olefins. The temperature at which the catalyst components are contacted with each other may fall between room temperature and the boiling point of the solvent used.

3. Olefin Polymerization Method

In the olefin polymerization method of the invention, olefins are polymerized in the presence of the catalyst mentioned above, optionally along with the component (C). The olefins include α-olefins such as ethylene, propylene, butene-1, octene-1, etc. Preferably, ethylene is polymerized. The mode of polymerization is not specifically defined, including, for example, solution reaction to be effected in a solvent, liquid-phase non-solvent reaction to be effected substantially in the absence of a solvent, vapor-phase reaction, etc. In the invention, any of those methods is employable. The reaction may be in any mode of continuous reaction or batch reaction. The solvent, if used, may be a hydrocarbon solvent such as pentane, hexane, heptane, cyclohexane, benzene, toluene, etc. One or more of these solvents may be used either singly or as combined. Regarding the amount of the catalyst to be used in the reaction in the presence of such a solvent, it is desirable that the amount of the component (A) falls generally between 0.1 and 100 μmols, but preferably between 1 and 20 μmols in one liter of the solvent, in view of the reaction activity. The reaction condition is not specifically defined. The reaction temperature may fall generally between −78 and 200° C., but preferably between room temperature and 150° C. The olefin pressure in the reaction system may fall generally between normal pressure and 15 MPa, but preferably between normal pressure and 8 MPa, more preferably between normal pressure and 5 MPa. The molecular weight of the product to be produced through the reaction may be controlled in any known manner, for example, by suitably changing the reaction temperature or pressure. According to the method of the invention, inexpensively produced are polyolefins having a molecular weight of over 10,000, and vinyl-terminated linear α-olefins, (referred to as oligomers) having a molecular weight of not larger than 10,000. The polyolefins and oligomers produced can be molded into various articles, or can be used for producing synthetic lubricant oils, detergents, etc.

The invention is described concretely with reference to the following Examples, which, however, are not whatsoever intended to restrict the scope of the invention.

First described are, the methods for analyzing the products produced through ethylene polymerization. The solid product produced is taken out through filtration, then dried at 120° C. for 12 hours, and thereafter weighed. The product which is gaseous at room temperature or the product soluble in a solvent is analyzed for its composition and purity through gas chromatography in the manner mentioned below.

(1) Composition Analysis

The product is analyzed through gas chromatography with Shimadzu's GC-14A Model equipped with an FID detector. The column is GL Science's TC-1 (length: 15 m, inner diameter 0.53 mm, film thickness 1.5 μm). The carrier gas is He. The temperature program is as follows: The sample charged into the column is kept at 40° C. for 5 minutes, then heated up to 320° C. at a heating rate of 10° C./min, and then kept at the elevated temperature for 10 minutes. The injector and the detector are both kept at 320° C. As so described in Examples, the internal standard is undecane.

(2) Analysis for Purity:

The product is analyzed through gas chromatography with Shimadzu's GC-14A Model equipped with an FID detector. The column is Hewlett-Packard's Ultra-2 (length: 25 m, inner diameter 0.20 mm, film thickness 0.33 μm). The carrier gas is He. The make-up gas is nitrogen. The temperature program is as follows: The sample charged into the column is heated from 90° C. up to 200° C. at a heating rate of 1.5° C./min, then immediately heated up to 200° C. at a heating rate of 8° C./min, and then kept at the elevated temperature for 70 minutes. The injector and the detector are both kept at 270° C.

The Cx purity (x is the number of carbons constituting the Cx fraction of the product) indicates the proportion (% by weight) of the normal-1-olefin existing in the Cx fraction of the product.

EXAMPLE 1

Preparation of Compound 3

(1) Ligand Preparation:

100 ml of methanol, 1.63 g of 2,6-diacetylpyridine (molecular weight 163.18; 10 mmols), 4.84 g of 2,4-dimethylaniline (molecular weight 121.18; 40 mmols) and 680 mg of 2,5-dimethyl-1,4-phenylenediamine (molecular weight 136.20; 5 mmols) were put into a 300 ml flask, and thoroughly stirred to prepare a homogenious mixture. 0.6 ml of formic acid was added to this, and further the mixture was stirred for 12 hours to make the compounds reacted completely. The resulting pale yellow crystal was taken out through filtration, washed with methanol, and dried under reduced pressure. Its $^1$H-NMR spectrum was assigned as the following product (molecular weight 632.85; 1.46 g, 2.3 mmols, yield 46%).

$^1$H-NMR [90 MHz, solvent: CDCl$_3$, based on tetramethylsilane (δ 0.00)]):

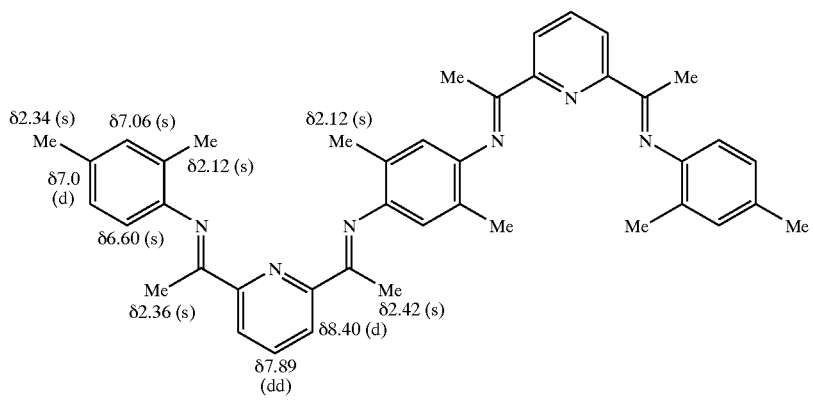

(2) Complex Preparation:

Next, a tetrahydrofuran solution (20 ml) of the ligand prepared herein (molecular weight 632.85; 633 mg, 1.0 mmol) and a tetrahydrofuran solution (20 ml) of ferrous(II) chloride tetrahydrate (formula weight 198.81; 437 mg, 2.2 mmols) were mixed in a 100 ml Schlenk tube and reacted for 12 hours in a nitrogen atmosphere. The resulting bluish violet solid was takenout through filtration, washed with tetrahydrofuran, and dried under reduced pressure. Thus was obtained the following complex, Compound 3 (molecular weight 886.35; 805 mg, 1.0 mmol, yield 100%).

the internal standard. The solid was taken out through filtration, dried at 120° C. for 12 hours, and then quantified. As a result, the overall weight of the product was 138 g. The oligomerization activity per the iron metal was 9870 kg/g-Fe·hr. The data of the composition analysis and the purity analysis of the product made according to the methods mentioned above are given in Table 1 and Table 2. In these Tables, Cx indicates the fraction having a carbon number, x. $C^+_{20}$ indicates the fraction having 20 or more carbon atoms. The heavy component is the solid polymer formed by polymerization.

(COMPOUND 3)

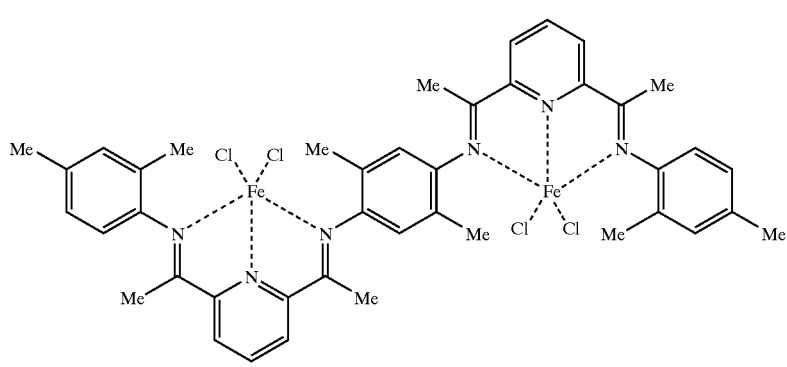

EXAMPLE 2

Ethylene Polymerization 250 ml of toluene and 0.5 ml of a toluene solution of polymethylaluminoxane (from Toso-Akzo, having a concentration of 1 mmol/ml) were put into a 1 liter autoclave, and 0.25 ml of a toluene suspension of Compound 3 (concentration: 1 μmol/ml) prepared in Example 1 was added thereto. 10 g of an internal standard, n-undecane was added thereto, and heated up to 50° C. After this was heated, ethylene was continuously introduced thereinto with its pressure being kept at 1.0 MPa, and reacted at 50° C. for 30 minutes. Next, an aqueous solution of sodium hydroxide (1 mol/liter) was added to the system to stop the reaction.

After the reaction, the autoclave was degassed, and the total volume of the gaseous component was measured with a wet flow meter. The gaseous component was analyzed to quantify the constituent components through gas chromatography. The α-olefin in the solution was quantitatively analyzed through gas chromatography using n-undecane as

EXAMPLE 3

Preparation of Compound 27

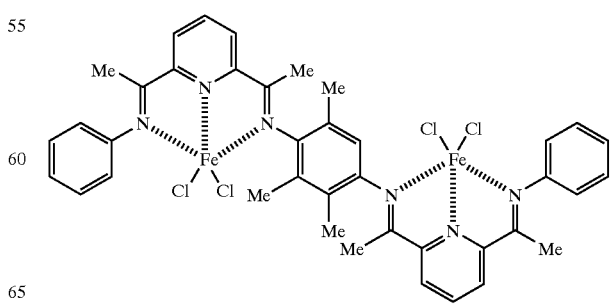

Compound 27

(1) Ligand Preparation:

100 ml of methanol, 19.6 g of 2,6-diacetylpyridine (molecular weight 163.18; 120 mmols) and 55.9 g of aniline (molecular weight 93.13; 600 mmols) were put into a 300 ml flask, and thoroughly stirred to prepare a homogeneous mixture. 0.6 ml of formic acid was added to this, and further the mixture was stirred at room temperature for 12 hours to make the compounds reacted completely. The resulting yellow crystal was taken out through filtration, washed with methanol, and dried under reduced pressure to obtain 34.5 g of 2,6-diacetylpyridine-diphenylimine (molecular weight 313.40; 110 mmols, yield 91%).

100 ml of tetrahydrofuran, 6.3 g (20 mmols) of 2,6-diacetylpyridine-diphenylimine and 0.82 g of 2,3,5,6-tetramethyl-1,4-phenylenediamine (molecular weight 164.25; 5 mmols) were put into a 300 ml flask, and thoroughly stirred to prepare a homogeneous mixture. 0.6 ml of formic acid was added to this, and further stirred at room temperature for 12 hours to make the compounds reacted completely. The resulting yellow crystal was taken out through filtration, washed with THF, and dried under reduced pressure. Its NMR spectrum was assigned as the intended ligand (molecular weight 604.79; 1.58 g, 2.6 mmols, yield 52%).

$^1$H-NMR [270 MHz, solvent: CDCl$_3$, based on chloroform (δ 7.24)]: δ 2.01 (12H, s), δ 2.27 (6H, s), δ 2.43 (6H, s), δ 6.86 (4H, d), δ 7.13 (2H, dd), δ 7.36–7.42 (4H, dd), δ 7.91 (2H, dd), δ 8.37 (2H, d), δ 8.50 (2H, d).

(2) Complex Preparation:

Next, the ligand prepared herein (molecular weight 604.79; 605 mg, 1.0 mmol), 10 ml of n-butanol, and ferrous(II) chloride 4-hydrate (formula weight 198.81; 437 mg, 2.2 mmols) were mixed in a 100 ml Schlenk tube and reacted at 80° C. for 30 minutes in a nitrogen atmosphere. The resulting solid was taken out through filtration, washed with hexane, and dried under reduced pressure. Thus was obtained the entitled complex, Compound 27 (molecular weight 858.30; 781 mg, 0.91 mmols, yield 91%).

EXAMPLE 4
Preparation of Compound 28

(COMPOUND 28)

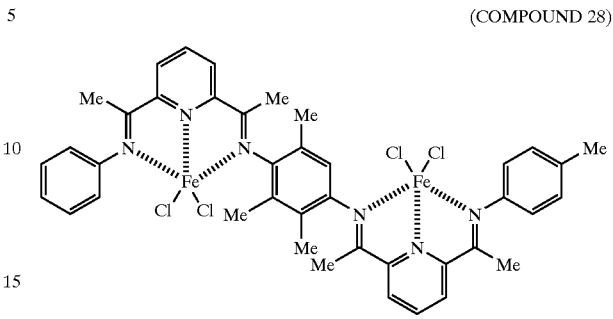

(1) Ligand Preparation:

100 ml of methanol, 9.8 g of 2,6-diacetylpyridine (molecular weight 163.18; 60 mmols) and 32.1 g of 4-methylaniline (molecular weight 107.15; 300 mmols) were put into a 300 ml flask, and thoroughly stirred to prepare a homogeneous mixture. 0.6 ml of formic acid was added to this, and further the mixture was stirred at room temperature for 4 hours to make the compounds reacted completely. The resulting yellow crystal was taken out through filtration, washed with methanol, and dried under reduced pressure to obtain 18.3 g of 2,6-diacetylpyridine-di(4-methylphenyl)imine (molecular weight 341.45; 53.6 mmols, yield 89%).

75 ml of tetrahydrofuran, 30 ml of methanol, 15.4 g (45 mmols) of 2,6-diacetylpyridine-di(4-methylphenyl)imine and 1.85 g of 2,3,5,6-tetramethyl-1,4-phenylenediamine (molecular weight 164.25; 11.3 mmols) were put into a 300 ml flask, and thoroughly stirred to prepare a homogeneous mixture. 0.6 ml of formic acid was added to this, and further stirred at 0° C. for 4 hours to make the compounds reacted completely. The resulting yellow crystal was taken out through filtration, washed with THF, and dried under reduced pressure. Its NMR spectrum was assigned as the intended ligand (molecular weight 632.85; 4.23 g, 6.7 mmols, yield 59%).

$^1$H-NMR [270 MHz, solvent: CDCl$_3$, based on chloroform (δ 7.24)]: δ 2.00 (12H, s), δ 2.22 (6H, s), δ 2.37 (6H, s), δ 2.43 (6H, s), δ 6.77 (4H, d), δ 7.20 (4H, d), δ 7.90 (2H, dd), δ 8.36 (2H, d), δ 8.49 (2H, d).

(2) Complex Preparation:

Next, the ligand prepared herein (molecular weight 632.85; 633 mg, 1.0 mmol) was processed in the same manner as in the step (2) in Example 3 to obtain the entitled complex, Compound 28 (molecular weight 886.34; 851 mg, 0.96 mmols, yield 96%).

EXAMPLE 5

Preparation of Compound 29

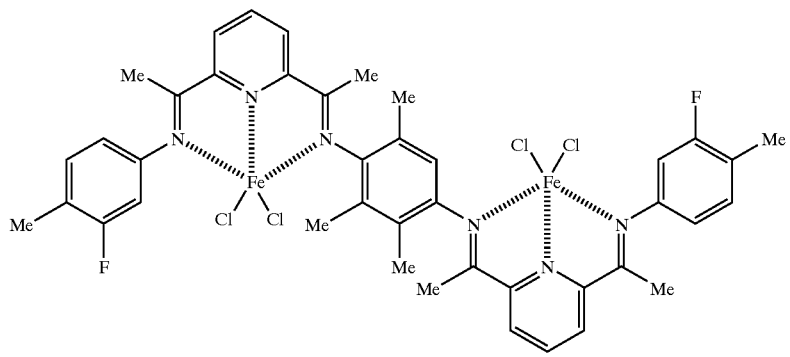

(COMPOUND 29)

(1) Ligand Preparation:

40 ml of toluene, 60 ml of cyclohexane, 7.84 g of 2,6-diacetylpyridine (molecular weight 163.18; 48 mmols) and 30.0 g of 3-fluoro-4-methylaniline (molecular weight 125.15; 240 mmols) were put into a 300 ml flask, and thoroughly stirred to prepare a homogeneous mixture. 0.5 g of sulfuric acid was added to this, and the mixture stirred for 4 hours under reflux to make the compounds reacted completely. Toluene and cyclohexane were removed in vacuum, and 20 ml of methanol was added to the residue to precipitate a white crystal. The crystal was taken out through filtration, washed with methanol, and dried under reduced pressure to obtain 5.74 g of 2,6-diacetylpyridine-di(3-fluoro-4-methylphenyl)imine (molecular weight 377.44; 15.2 mmols, yield 31%).

12 ml of tetrahydrofuran, 36 ml of methanol, 4.53 g (12 mmols) of 2,6-diacetylpyridine-di(3-fluoro-4-methylphenyl)imine and 657 mg of 2,3,5,6-tetramethyl-1,4-phenylenediamine (molecular weight 164.25; 3.0 mmols) were put into a 100 ml flask, and thoroughly stirred to prepare a homogeneous mixture. 0.3 ml of formic acid was added to this, and further stirred at 0° C. for 4 hours to make the compounds reacted completely. The resulting yellow crystal was taken out through filtration, washed with methanol, and dried under reduced pressure. Its NMR spectrum was assigned as the intended ligand (molecular weight 668.83; 1.42 g, 2.12 mmols, yield 71%).

$^1$H-NMR (270 MHz, solvent: CDCl$_3$, based on chloroform (δ 7.24)]: δ 2.00 (12H, s), δ 2.25 (6H, s), δ 2.29 (6H, s), δ 2.44 (6H, s), δ 6.54–6.58 (4H, d), δ 7.18 (2H, t), δ 7.91 (2H, dd), δ 8.34 (2H, d), δ 8.50 (2H, d).

(2) Complex Preparation:

Next, the ligand prepared herein (molecular weight 668.83; 669 mg, 1.0 mmol) was processed in the same method as in the step (2) in Example 3 to obtain the entitled complex, Compound 29 (molecular weight 922.34; 774 mg, 0.84 mmols, yield 84%).

EXAMPLE 6

Preparation of Compound 30

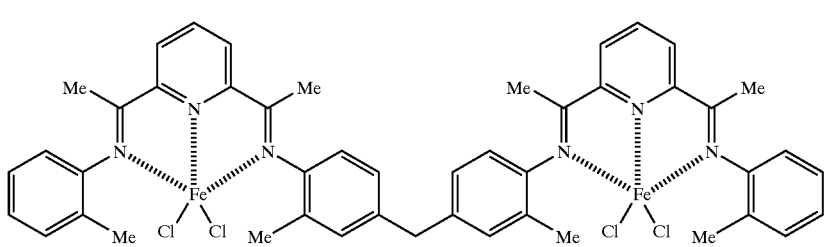

(COMPOUND 30)

(1) Ligand Preparation:

100 ml of methanol, 6.53 g of 2,6-diacetylpyridine (molecular weight 163.18; 40 mmols) and 21.4 g of 2-methylaniline (molecular weight 107.15; 200 mmols) were put into a 300 ml flask, and thoroughly stirred to prepare a homogeneous mixture. 0.6 ml of formic acid was added to this, and the mixture was stirred at room temperature for 4 hours to make the compounds reacted completely. The resulting yellow crystal was taken out through filtration, washed with methanol, and dried under reduced pressure to obtain 10.3 g of 2,6-diacetylpyridine-di(2-methylphenyl)imine (molecular weight 341.45; 30.3 mmols, yield 76%).

10 ml of tetrahydrofuran, 20 ml of methanol, 5.1 g (15 mmols) of 2,6-diacetylpyridine-di(2-methylphenyl)imine and 850 mg of 4,4'-diamino-3,3'-dimethyldiphenylmethane (molecular weight 226.32; 3.75 mmols) were put into a 100 ml flask, and thoroughly stirred to prepare a homogeneous mixture. 0.6 ml of formic acid was added to this, and further stirred at 0° C. for 4 hours to make the compounds reacted completely. The resulting yellow crystal was taken out through filtration, washed with methanol, and dried under reduced pressure. Its NMR spectrum was assigned as the intended ligand (molecular weight 694.92; 1.25 g, 1.8 mmols, yield 48%).

$^1$H-NMR (270 MHz, solvent: CDCl$_3$, based on chloroform (δ 7.24)]: δ 2.12 (12H), δ 2.34 (6H, s), δ 2.37 (6H, s), δ 6.64 (2H, d), δ 6.69 (2H, d), δ 7.01–7.10 (6H, m), δ 7.18–7.26 (4H, m), δ 7.89 (2H, dd), δ 8.40 (4H, d).

(2) Complex Preparation:

Next, the ligand prepared herein (molecular weight 694.92; 695 mg, 1.0 mmol) was processed in the same method as in the step (2) in Example 3 to obtain the entitled complex, Compound 30 (molecular weight 948.43; 871 mg, 0.92 mmols, yield 92%).

EXAMPLE 7

Preparation of Compound 31

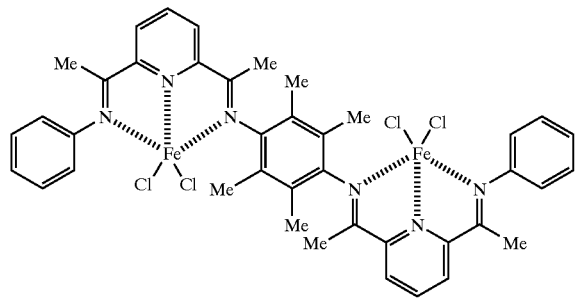

(1) Ligand Preparation:

100 ml of methanol, 19.6 g of 2,6-diacetylpyridine (molecular weight 163.18; 120 mmols) and 55.9 g of aniline (molecular weight 93.13; 600 mmols) were put into a 300 ml flask, and thoroughly stirred to prepare a homogeneous mixture. 0.6 ml of formic acid was added to this, and the mixture was stirred at room temperature for 12 hours to make the compounds reacted completely. The resulting yellow crystal was taken out through filtration, washed with methanol, and dried under reduced pressure to obtain 34.5 g of 2,6-diacetylpyridine-diphenylimine (molecular weight 313.40; 110 mmols, yield 91%). Next, 35 ml of tetrahydrofuran, 20 ml of methanol, 1.57 g (5 mmols) of 2,6-diacetylpyridine-diphenylimine prepared herein, and 170 mg of 2,5-dimethyl-1,4-phenylenediamine (molecular weight 136.20; 1.25 mmols) were put into a 100 ml flask, and thoroughly stirred to prepare a homogeneous mixture. 0.3 ml of formic acid was added to this, and further stirred at −20° C. for 7 hours to make the compounds reacted completely. The resulting yellow crystal was taken out through filtration, washed with methanol, and dried under reduced pressure. Its NMR spectrum was assigned as the intended ligand (molecular weight 576.74; 320 mg, 0.56 mmols, yield 44%).

$^1$H-NMR [270 MHz, solvent: $CDCl_3$, based on chloroform ($\delta$ 7.24)]: $\delta$ 2.13 (6H, s), $\delta$ 2.43 (6H, s), $\delta$ 6.61 (2H, s), $\delta$ 6.87 (4H, d), $\delta$ 7.14 (2H, dd), $\delta$ 7.87–7.93 (2H, dd), $\delta$ 8.34–8.44 (4H, dd).

(2) Complex Preparation:

Next, the ligand prepared herein (molecular weight 576.74; 577 mg, 1.0 mmol) was processed in the same method as in the step (2) in Example 3 to obtain the entitled complex, Compound 31 (molecular weight 830.25; 792 mg, 0.95 mmols, yield 95%).

EXAMPLE 8

Ethylene Polymerization

The same process of ethylene polymerization as in Example 2 was repeated, except that 2 ml of a toluene suspension of Compound 27 (0.5 μmols/ml) and not Compound 3 was used herein.

EXAMPLE 9

Ethylene Polymerization

The same process of ethylene polymerization as in Example 2 was repeated, except that 2 ml of a toluene suspension of Compound 28 (0.5 μmol/ml) and not Compound 3 was used herein.

EXAMPLE 10

Ethylene Polymerization

The same process of ethylene polymerization as in Example 2 was repeated, except that 2 ml of a toluene suspension of Compound 29 (0.5 μmol/ml) and not Compound 3 was used herein.

EXAMPLE 11

Ethylene Polymerization

The same process of ethylene polymerization as in Example 2 was repeated, except that 2 ml of a toluene suspension of Compound 30 (0.5 μmol/ml) and not Compound 3 was used herein.

EXAMPLE 12

Ethylene Polymerization

The same process of ethylene polymerization as in Example 2 was repeated, except that 2 ml of a toluene suspension of Compound 31 (0.5 μmol/ml) and not Compound 3 was used herein.

The data of α-olefin distribution and purity in Examples 8 to 12 are given in Table 1 and Table 2.

EXAMPLE 13

Preparation of Compound 34

(1) Ligand Preparation:

100 ml of methanol, 1.63 g of 2,6-diacetylpyridine (molecular weight 163.18; 10 mmols), 4.84 g of 2,4-dimethylaniline (molecular weight 121.18; 40 mmols) and 540 mg of 1,4-phenylenediamine (molecular weight 108.14; 5 mmols) were put into a 300 ml flask, and thoroughly stirred to prepare a homogeneous mixture. 0.6ml of formic acid was added to this, and further the mixture was stirred for 12 hours to make the compounds reacted completely. The resulting pale yellow crystal was taken out through filtration, washed with methanol, and dried under reduced pressure. Its $^1$H-NMR spectrum was assigned as the following product (molecular weight 604.80; 1.78 g, 2.95 mmols, yield 59%).

$^1$H-NMR [90 MHz, solvent: $CDCl_3$, based on tetramethylsilane ($\delta$ 0.00)]:

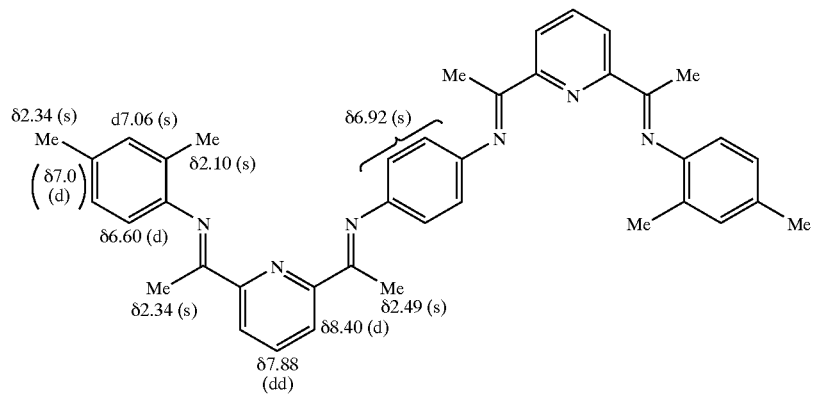

benzene ring region: δ 6.5–7.2

(2) Complex Preparation:

Next, a tetrahydrofuran solution (20 ml) of the ligand prepared herein (molecular weight 604.80; 605 mg; 1.0 mmol) and a tetrahydrofuran solution (20 ml) of ferrous (II) chloride 4-hydrate (formula weight 198.81; 437 mg, 2.2 mmols) were mixed in a 100 ml Schlenk tube and reacted for 12 hours in a nitrogen atmosphere. The resulting bluish violet solid was taken out through filtration, washed with tetrahydrofuran, and dried under reduced pressure. Thus was obtained a complex, Compound 34 mentioned above (molecular weight 858.30; 810 mg, 0.94 mmols, yield 94%).

was 59 g. The oligomerization activity per the iron metal was 1054 kg/g-Fe·hr. The data of the composition analysis and the purity analysis of the product made according to the methods mentioned above are given in Table 1 and Table 2. In these Tables, Cx indicates the fraction having a carbon number, x. $C^+_{20}$ indicates the fraction having 20 or more carbon atoms. The heavy component is the solid polymer formed by polymerization.

EXAMPLE 15

Preparation of Compound 46

(COMPOUND 46)

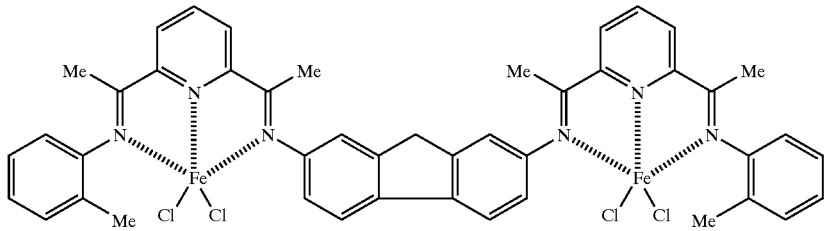

EXAMPLE 14

Ethylene Polymerization 250 ml of toluene and 2.0 ml of a toluene solution of polymethylaluminoxane (from Toso-Akzo, having a concentration of 1 mmol/ml) were put into a 1 liter autoclave, and 2.0 ml of a toluene suspension of Compound 34 (concentration: 0.5 μmol/ml) prepared in the above was added thereto. 10 g of an internal standard, n-undecane was added thereto, and heated up to 50° C. After this was heated, ethylene was continuously introduced thereinto with its pressure being kept at 1.0 MPa, and reacted at 50° C. for 30 minutes. Next, an aqueous solution of sodium hydroxide (1 mol/liter) was added to the system to stop the reaction.

After the reaction, the autoclave was degassed, and the total volume of the gaseous component was measured with a wet flow meter. The gaseous component was analyzed to quantify the constituent components through gas chromatography. The α-olefin in the solution was quantitatively analyzed through gas chromatography using n-undecane as the internal standard. No solid was detected in the product obtained herein. As a result, the overall weight of the product (1) Ligand Preparation:

100 ml of methanol, 6.53 g of 2,6-diacetylpyridine (molecular weight 163.18; 40 mmols) and 21.4 g of 2-methylaniline (molecular weight 107.15; 200 mmols) were put into a 300 ml flask, and thoroughly stirred to prepare a homogeneous mixture. 0.6 ml of formic acid was added to this, and further the mixture was stirred at room temperature for 4 hours to make the compounds reacted completely. The resulting yellow crystal was taken out through filtration, washed with methanol, and dried under reduced pressure to obtain 10.3 g of 2,6-diacetylpyridine-di (2-methylphenyl)imine (molecular weight 341.45; 30.3 mmols, yield 76%) Next, 10 ml of tetrahydrofuran, 20 ml of methanol, 5.1 g (15 mmols) of 2,6-diacetylpyridine-di(2-methylphenyl)imine and 1.96 g of 2,7-diaminofluorenone (molecular weight 196.25; 10 mmols) were put into a 100 ml flask, and thoroughly stirred to prepare a homogeneous mixture. 0.6 ml of formic acid was added to this, and further the mixture was stirred at room temperature for 4 hours to make the compounds reacted completely. The resulting yellow crystal was taken out through filtration, washed with methanol, and dried under reduced pressure. Its NMR spectrum was assigned as the intended ligand (molecular weight 664.84; 2.65 g, 4.0 mmols, yield 53%).

¹H-NMR [270 MHz, solvent: CDCl₃, based on chloroform (δ 7.24)]: δ 2.14 (6H, s), δ 2.35–2.48 (12H), δ 3.97 (2H, s), δ 6.71 (2H, d), δ 6.89 (2H, d), δ 7.02–7.06 (4H, m), δ 7.19–7.26 (4H, m), δ 7.77 (2H, d), δ 7.91 (2H, dd), δ 8.40 (4H, dd).

(2) Complex Preparation:

Next, the ligand prepared herein (molecular weight 664.84; 665 mg, 1.0 mmol), 10 ml of n-butanol, and ferrous(II) chloride 4-hydrate (formula weight 198.81; 437 mg, 2.2 mmols) were mixed in a 100 ml Schlenk tube and reacted at 80° C. for 30 minutes in a nitrogen atmosphere. The resulting solid was taken out through filtration, washed with hexane, and dried under reduced pressure. Thus was obtained the entitled complex, Compound 46 (molecular weight 918.35; 848 mg, 0.92 mmols, yield 92%).

EXAMPLE 16

Preparation of Compound 47

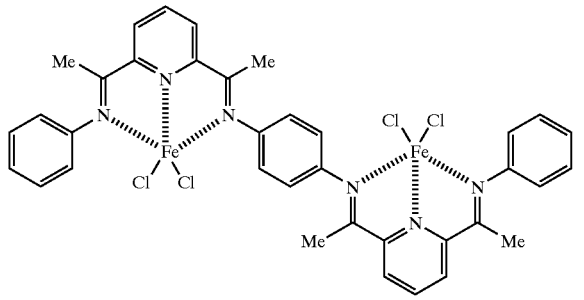

(COMPOUND 47)

(1) Ligand Preparation:

100 ml of methanol, 19.6 g of 2,6-diacetylpyridine (molecular weight 163.18; 120 mmols) and 55.9 g of aniline (molecular weight 93.13; 600 mmols) were put into a 300 ml flask, and thoroughly stirred to prepare a homogeneous mixture. 0.6 ml of formic acid was added to this, and further the mixture was stirred at room temperature for 12 hours to make the compounds reacted completely. The resulting yellow crystal was taken out through filtration, washed with methanol, and dried under reduced pressure to obtain 34.5 g of 2,6-diacetylpyridine-diphenylimine (molecular weight 313.40; 110 mmols, yield 91%). Next, 50 ml of tetrahydrofuran, 4.70 g (15 mmols) of 2,6-diacetylpyridine-diphenylimine prepared herein, and 406 mg of 1,4-phenylenediamine (molecular weight 108.14; 3.75 mmols) were put into a 100 ml flask, and thoroughly stirred to prepare a homogeneous mixture. 0.3 ml of formic acid was added to this, and further the mixture was stirred at room temperature for 4 hours to make the compounds reacted completely. The resulting yellow crystal was taken out through filtration, washed with tetrahydrofuran, and dried under reduced pressure. Its NMR spectrum was assigned as the intended ligand (molecular weight 548.68; 1.75 g, 3.19 mmols, yield 85%).

¹H-NMR [270 MHz, solvent: CDCl₃, based on chloroform (δ 7.24)]: δ 2.42 (6H, s), δ 2.49 (6H, s), δ 6,86 (4H, d), δ 6.92 (4H, d), δ 7.13 (2H, dd), δ 7.39 (4H, dd), δ 7.89 (2H, dd), δ 8.34–8.37 (4H).

(2) Complex Preparation:

The ligand prepared herein (molecular weight 548.68; 549 mg, 1.0 mmol) was processed in the same manner as in the step (2) in Example 15 to obtain the entitled complex, Compound 47 (molecular weight 802.19; 723 mg, 0.90 mmols, yield 90%).

EXAMPLE 17

Ethylene Polymerization

The same process of ethylene polymerization as in Example 14 was repeated, except that 2 ml of a toluene suspension of Compound 46 (0.5 μmols/ml) and not Compound 34 was used herein.

EXAMPLE 18

Ethylene Polymerization

The same process of ethylene polymerization as in Example 14 was repeated, except that 2 ml of a toluene suspension of Compound 47 (0.5 μmol/ml) and not Compound 34 was used herein.

The data of α-olefin distribution and purity in Examples 17 and 18 are given in Table 1 and Table 2.

COMPARATIVE EXAMPLE 1

Preparation of Iron Dichloride/[2,6-diacetylpyridine-bis(2,4-dimethylphenylimine)] Complex (1) Ligand Preparation: Preparation of 2,6-diacetylpyridine-bis(2,4-dimethylphenylimine)

100 ml of methanol, 1.63 g of 2,6-diacetylpyridine (molecular weight 163.18; 10 mmols), and 4.84 g of 2,4-dimethylaniline (molecular weight 121.18; 40 mmols) were put into a 300 ml flask, and thoroughly stirred to prepare a homogeneous mixture. 0.6 ml of formic acid was added to this, and further the mixture was stirred for 12 hours to make the compounds reacted completely. The reaction mixture was left at −78° C. for 1 hour, and the resulting pale yellow crystal was taken out through filtration, washed with methanol, and dried under reduced pressure. Its ¹H-NMR spectrum was assigned as the intended product, 2,6-diacetylpyridine-bis(2,4-dimethylphenylimine) (molecular weight 369.52; 1.60 g, 4.33 mmols, yield 43%).

¹H-NMR [90 MHz, solvent: CDCl₃, based on tetramethylsilane (δ 0.00)]: δ 2.10 (6H, 2-CH₃, s), δ 2.34 (6H, 4-CH₃, s), δ 2.34 (6H, imine-CH₃, s), δ 6.5–7.2 (6H, benzene ring), δ 7.87 (1H, p-pyridine ring, dd), δ 8.40 (2H, m-pyridine ring, d).

(2) Complex Preparation: Preparation of Iron Dichloride/[2,6-diacetylpyridine-bis(2,4-dimethylphenylimine)]Complex Next, a tetrahydrofuran solution (40 ml) of 2,6-diacetylpyridine-bis(2,4-dimethylphenylimine) prepared herein (molecular weight 369.52; 1.0 g, 2.71 mmols), and a tetrahydrofuran solution (40 ml) of ferrous(II) chloride 4-hydrate (formula weight 198.81; 497mg, 2.5mmols) were mixed in a 100 ml Schlenk tube and reacted for 12 hours in a nitrogen atmosphere. The resulting bluish violet solid was taken out through filtration, washed with tetrahydrofuran, and dried under reduced pressure. Thus was obtained a complex mentioned below (molecular weight 496.27; 1.24 g, 2.5mmols, yield 100%).

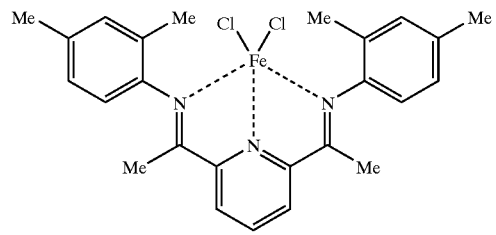

(3) Ethylene Polymerization:

250 ml of toluene and 1.0 ml of a toluene solution of polymethylaluminoxane (from Toso-Akzo, having a concentration of 1 mmol/ml) were put into a 1 liter autoclave, and 0.5 ml of a toluene suspension of the ligand (concentration: 1 µmol/ml) prepared in the above was added thereto. 10 g of an internal standard, n-undecane was added thereto, and heated up to 50° C. After this was heated, ethylene was continuously introduced thereinto with its pressure being kept at 1.0 MPa, and reacted at 50° C. for 30 minutes. Next, an aqueous solution of sodium hydroxide (1 mol/liter) was added to the system to stop the reaction.

After the reaction, the autoclave was degassed, and the total volume of the gaseous component was measured with a wet flow'meter. The gaseous component was analyzed to quantify the constituent components through gas chromatography. The α-olefin in the solution was quantitatively analyzed through gas chromatography using n-undecane as the internal standard. The solid was taken out through filtration, dried at 120° C. for 12 hours, and then quantified. As a result, the overall weight of the product was 72 g. The oligomerization activity per the iron metal was 5200 kg/g-Fe-hr. The data of the composition analysis and the purity analysis of the product made according to the methods mentioned above are given in Table 1 and Table 2.

TABLE 2

| | Product Purity | | |
|---|---|---|---|
| | Purity (% by weight) | | |
| Example | $C_{14}$ | $C_{16}$ | $C_{18}$ |
| 2 | 95.46% | 94.86% | 94.17% |
| 8 | 97.94% | 97.72% | 97.44% |
| 9 | 98.07% | 97.70% | 97.48% |
| 10 | 98.00% | 97.67% | 97.49% |
| 11 | 91.94% | 90.92% | 89.82% |
| 12 | 86.88% | 88.34% | no data |
| 14 | 84.74% | 83.06% | 82.30% |
| 17 | 82.19% | 83.16% | 85.38% |
| 18 | 63.79% | 67.73% | 75.15% |
| *1 | 96.55% | 95.62% | 94.95% |

*indicates Comparative Example.

According to the invention, efficiently produced are vinyl-terminated linear α-olefins (oligomers) having a molecular weight of not larger than 10,000, and polyolefins having a molecular weight of over 10,000.

What is claimed is:

1. A transition metal compound of Groups 8 to 10 of the Periodic Table, represented by the following formula (1):

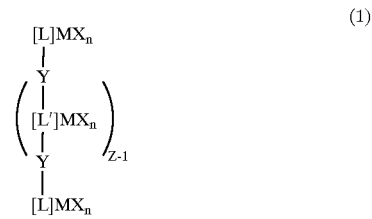

TABLE 1

| | | | Composition Distribution of Product | | | | | | | | | |
|---|---|---|---|---|---|---|---|---|---|---|---|---|
| | Overall | Activity | Composition (% by weight) | | | | | | | | | |
| Example | Weight of Product (g) | (kg/g-Fe-hr) | $C_4$ | $C_6$ | $C_8$ | $C_{10}$ | $C_{12}$ | $C_{14}$ | $C_{16}$ | $C_{18}$ | $C_{20}+$ | heavy component |
| 2 | 138 | 9870 | 11.6 | 11.6 | 10.5 | 8.3 | 6.7 | 5.4 | 4.4 | 3.7 | 17.7 | 20.2 |
| 8 | 124 | 8849 | 13.4 | 12.8 | 11.2 | 8.5 | 6.5 | 5.0 | 4.0 | 3.3 | 13.1 | 22.3 |
| 9 | 96 | 6893 | 9.1 | 9.3 | 8.7 | 7.0 | 5.8 | 4.8 | 3.9 | 3.4 | 17.9 | 30.1 |
| 10 | 81 | 5791 | 8.9 | 9.2 | 8.5 | 7.0 | 5.8 | 4.8 | 3.9 | 3.4 | 17.5 | 31.0 |
| 11 | 188 | 13454 | 17.5 | 15.5 | 12.5 | 8.7 | 6.3 | 4.5 | 3.4 | 2.7 | 11.3 | 17.6 |
| 12 | 26 | 1884 | 35.1 | 23.9 | 15.8 | 7.4 | 4.2 | 2.5 | 1.6 | 1.1 | 2.8 | 5.4 |
| 14 | 59 | 1054 | 31.7 | 23.9 | 16.3 | 9.9 | 6.0 | 3.6 | 2.4 | 1.6 | 4.5 | 0.0 |
| 17 | 19 | 464 | 35.3 | 24.8 | 16.2 | 8.6 | 4.9 | 2.9 | 1.7 | 1.2 | 2.5 | 1.8 |
| 18 | 20 | 1418 | 57.3 | 25.6 | 11.3 | 3.3 | 1.3 | 0.5 | 0.2 | 0.1 | 0.1 | 0.3 |
| *1 | 72 | 5200 | 8.4 | 9.2 | 9.0 | 8.0 | 6.9 | 6.0 | 5.2 | 4.5 | 20.2 | 20.7 |

*indicates Comparative Example.

wherein M represents a transition metal of Groups 8 to 10 of the Periodic, Table; L, electrically neutral, represents a hetero atom-containing hydrocarbon group represented by the following formula (2)

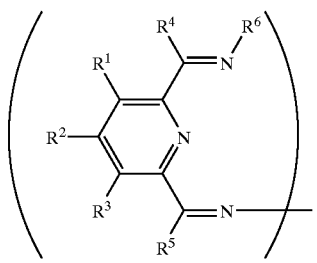

(2)

wherein $R^1$ to $R^5$ each independently represent a hydrogen atom, a halogen atom, a hydrocarbon group having from 1 to 20 carbon atoms, a halogenohydrocarbon group having form 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group;

L', electrically neutral, represent a hetero atom-containing hydrocarbon group represented by the following formula (3)

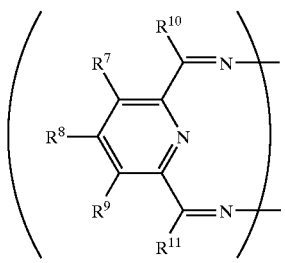

(3)

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring;

X represents a covalent-bonding or ionic-bonding group, and a plurality of X's are the same or different; Y represents an aromatic group-containing crosslinking group; Z is an integer of 1 or more, indicating the degree of polymerization of the compound; n indicates the atomic valency of M; and each M, L, and Y are the same or different.

2. The transition metal compound as claimed in claim 1, wherein the transition metal M is iron or cobalt.

3. A transition metal compound of the following formula (4):

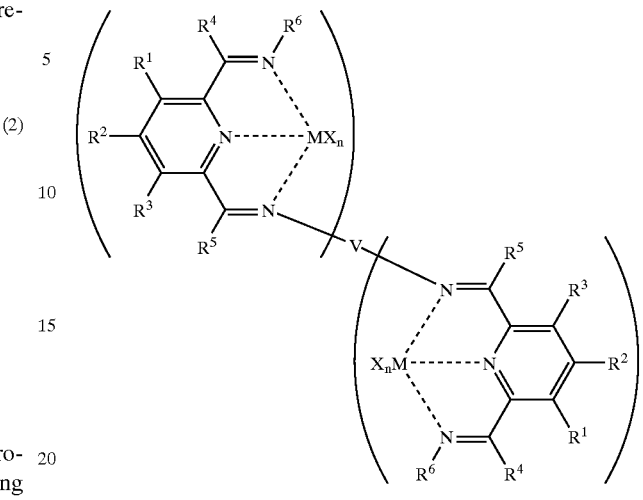

(4)

wherein V is a crosslinking group that is represented by the following formula (5A) or (5B):

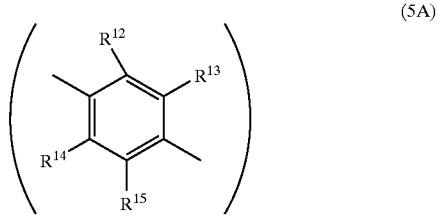

(5A)

wherein M represents a transition metal of Groups 8 to 10 of the Periodic Table; $R^1$ to $R^5$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group; X represents a covalent-bonding or ionic-bonding group, and a plurality of X's are the same or different; n indicates the atomic valency of M; $R^{12}$ to $R^{15}$, and $R^{16}$ to $R^{23}$ each independently represent a hydrogen atom, or a hydrocarbon group having from 1 to 20 carbon atoms, and optionally these groups are the same or different; $R^{16}$ and $R^{23}$ optionally are bonded to each other to form a ring; B represents $—(R^{24}{}_2C)_m—$, $—R^{24}{}_2Si—$, $—O—$, $—S—$, or $—R^{24}N—$; $R^{24}$ represents a hydrogen atom, or a hydrocarbon group having from 1 to 20 carbon atoms; and m is an integer of from 0 to 4.

4. The transition metal compound as claimed in claim 3, wherein the transition metal M is iron or cobalt.

5. The transition metal compound as claimed in claim 3, wherein $R^{12}$ and $R^{15}$ each are at hydrocarbon group having from 1 to 20 carbon atoms, and $R^{13}$ and $R^{14}$ are both hydrogen atoms.

6. The transition metal compound as claimed in claim 3, wherein $R^6$ is a group represented by the following formula:

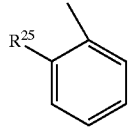

wherein $R^{25}$ is a methyl group, ethyl group or a hydrogen atom.

7. An olefin polymerization catalyst comprising the following (A) and (B):

(A) a transition metal compound represented by the following formula (1):

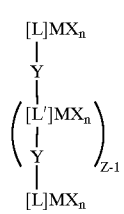

wherein M represent a transition metal of Groups 8 to 10 of the Periodic Table; L, electrically neutral, represents a hetero atom-containing hydrocarbon group represented by the following formula (2)

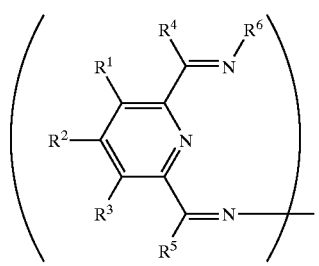

wherein $R^1$ to $R^5$ each independently represent a hydrogen atom, a halogen atom, a hydrocarbon group having from 1 to 20 carbon atoms, a halogenohydrocarbon group having form 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group;

L', electrically neutral, represent a hetero atom-containing hydrocarbon group represented by the following formula (3)

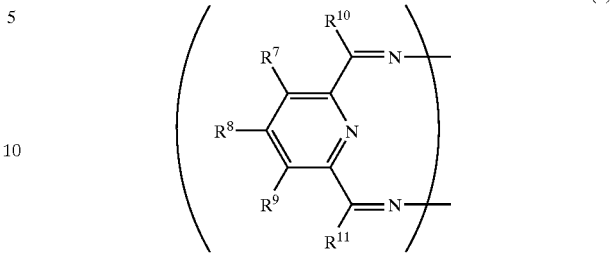

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring;

X represents a covalent-bonding or ionic-bonding group, and a plurality of X's are the same or different; Y represents an aromatic group-containing crosslinking group; Z is an integer of 1 or more, indicating the degree of polymerization of the compound; n indicates the atomic valency of M; and each M, L, and Y are the same or different;

(B) at least one compound selected from the group consistist of (B-1) organoaluminium compounds, (B-2) ionic compounds capable of converting the transition metal compound into a cationic transition metal compound, (B-3) Lewis acids, and (B4) clay, clay minerals and ion-exchanging layered compounds.

8. The olefin polymerization catalyst as claimed in claim 7, wherein the component (B) is any one of an alkylaluminoxane, a boron compound and a phyllosilicic acid compound.

9. A method for olefin polymerization, which comprises: polymerizing an olefin in the presence of the olefin polymerization catalyst of claim 7.

10. The olefin polymerization catalyst as claimed in claim 7, wherein the component (A) is the transition metal compound of Groups 8 to 10 of the Periodic Table, represented by the following formula (1)

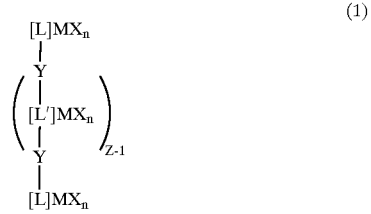

wherein M represent a transition metal of Groups 8 to 10 of the Periodic Table; L, electrically neutral, represents a hetero atom-containing hydrocarbon group represented by the following formula (2)

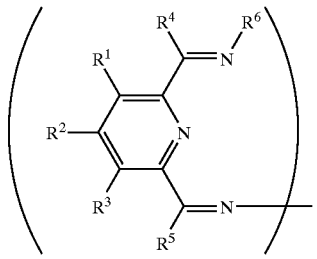

(2)

wherein $R^1$ to $R^5$ each independently represent a hydrogen atom, a halogen atom, a hydrocarbon group having from 1 to 20 carbon atoms, a halogenohydrocarbon group having form 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group;

L', electrically neutral, represent a hetero atom-containing hydrocarbon group represented by the following formula (3)

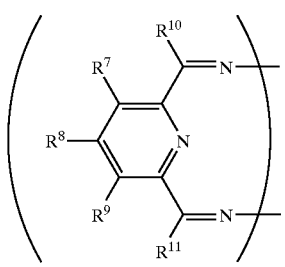

(3)

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring;

X represents a covalent-bonding or ionic-bonding group, and a plurality of X's are the same or different; Y represents an aromatic group-containing crosslinking group; Z is an integer of 1 or more, indicating the degree of polymerization of the compound; n indicates the atomic valency of M; and each M, L, and Y are the same or different; or the following formula (4):

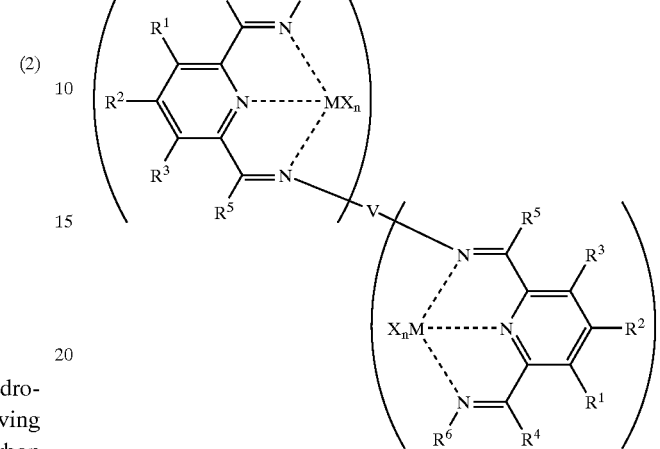

(4)

wherein V is a crosslinking group that is represented by the following formula (5A) or (5B):

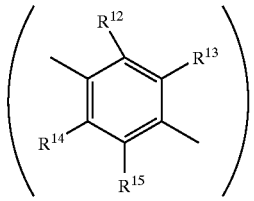

(5A)

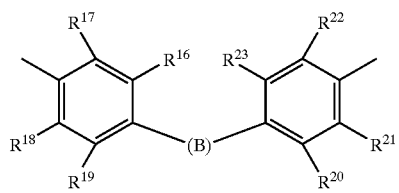

(5B)

wherein M represents a transition metal of Groups 8 to 10 of the Periodic Table; $R^1$ to $R^5$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group; X represents a covalent-bonding or ionic bonding group, and a plurality of X's are the same or different; n indicates the atomic valency of M; $R^{12}$ to $R^{15}$, and $R^{16}$ to $R^{23}$ each independently represent a hydrogen atom, or a hydrocarbon group having from 1 to 20 carbon atoms, and optionally these groups are the same or different; $R^{16}$ and $R^{23}$ optionally are bonded to each other to form a ring; B represents $-(R^{24}{}_2C)_m-$, $-R^{24}{}_2Si-$, $-O-$, $-S-$, or $-R^{24}N-$; $R^{24}$ represents a hydrogen atom, or a hydrocarbon group having from 1 to 20 carbon atoms; and m is an integer of from 0 to 4.

11. An olefin polymerization catalyst comprising the following (A), (B) ad (C)

(A) a transition metal compound represented by the following formula (1):

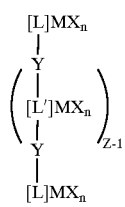

wherein M represent a transition metal of Groups 8 to 10 of the Periodic Table; L, electrically neutral, represents a hetero atom-containing hydrocarbon group represented by the following formula (2)

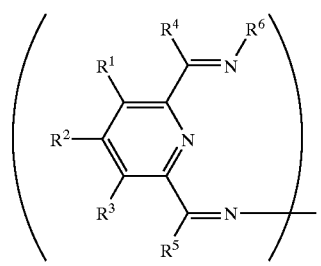

wherein $R^1$ to $R^5$ each independently represent a hydrogen atom, a halogen atom, a hydrocarbon group having from 1 to 20 carbon atoms, a halogenohydrocarbon group having form 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group;

L', electrically neutral, represent a hetero atom-containing hydrocarbon group represented by the following formula (3)

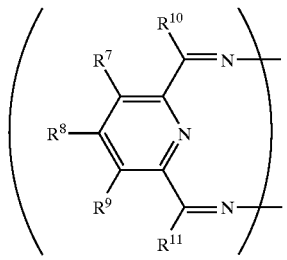

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring;

X represents a covalent-bonding or ionic-bonding group, and a plurality of X's are the same or different; Y represents an aromatic group-containing crosslinking group; Z is an integer of 1 or more, indicating the degree of polymerization of the compound; n indicates the atomic valency of M; and each M, L, and Y are the same or different;

(B) at least one compound selected from the group consistist of (B-1) organoaluminium compounds, (B-2) ionic compounds capable of converting the transition metal compound into a cationic transition metal compound, (B-3) Lewis acids, and (B4) clay, clay minerals and ion-exchanging layered compounds.

(C) an organometallic compound.

12. A method for olefin polymerization, which comprises polymerizing an olefin in the presence of the olefin polymerization catalyst of claim 11.

13. The olefin polymerization catalyst as claimed in claim 7, wherein the component (B) is any one of an alkylaluminoxane, boron compound and a phyllosilicic acid compound.

14. The olefin polymerization catalyst as claimed in claim 11, wherein the component (A) is the transition metal compound of Groups 8 to 10 of the Periodic Table, represented by the following formula (1)

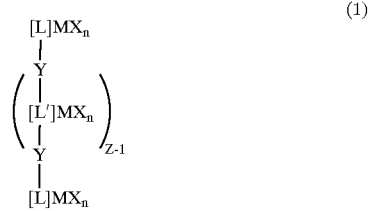

wherein M represent a transition metal of Groups 8 to 10 of the Periodic Table; L, electrically neutral, represents a hetero atom-containing hydrocarbon group represented by the following formula (2)

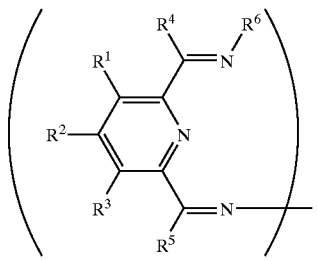

wherein $R^1$ to $R^5$ each independently represent a hydrogen atom, a halogen atom, a hydrocarbon group having from 1 to 20 carbon atoms, a halogenohydrocarbon group having form 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group;

L' electrically neutral, represent a hetero atom-containing hydrocarbon group represented by the following formula (3)

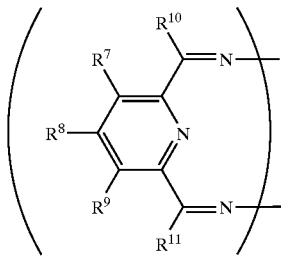

wherein $R^7$ to $R^{11}$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring;

X represents a covalent-bonding or ionic-bonding group, and a plurality of X's, are the same or different; Y represents an aromatic group-containing crosslinking group; Z is an integer of 1 or more, indicating the degree of polymerization of the compound; n indicates the atomic valency of M; and each M, L, and Y are the same or different; or the following formula (4):

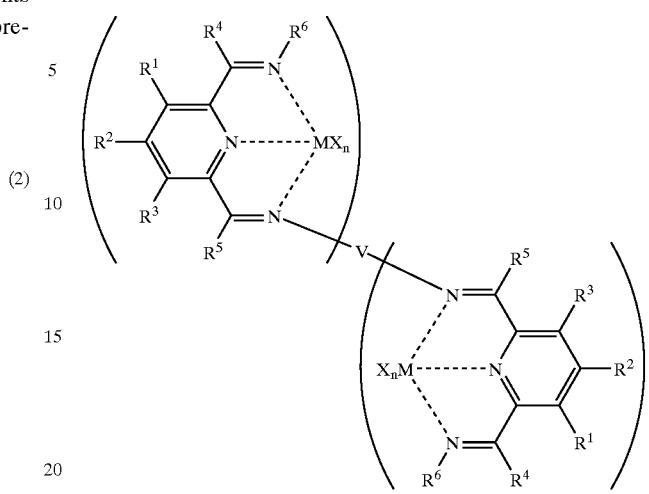

wherein V is a crosslinking group that is represented by the following formula (5A) or (5B):

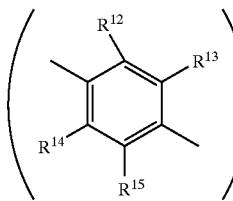

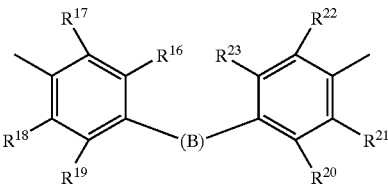

wherein M represents a transition metal of Groups 8 to 10 of the Periodic Table; $R^1$ to $R^5$ each independently represent a hydrogen atom, a halogen atom, a hydrocarbon group having from 1 to 20 carbon atoms, a halogenohydrocarbon group having from 1 to 20 carbon atoms, or a hetero atom-containing group, and optionally these groups are bonded to each other to form a ring; $R^6$ represents a hydrogen atom, a hydrocarbon group having from 1 to 40 carbon atoms, a halogenohydrocarbon group having from 1 to 40 carbon atoms, or a hetero atom-containing group; X represents a covalent-bonding or ionic-bonding group, and a plurality of X's are the same or different; n indicates the atomic valency of M; $R^{12}$ to $R^{15}$, and $R^{16}$ to $R^{23}$ each independently represent a hydrogen atom, or a hydrocarbon group having from 1 to 20 carbon atoms, and optionally these groups are the same or different; $R^{16}$ and $R^{23}$ optionally are bonded to each other to form a ring; B represents $-(R^{24}{}_2C)_m-$, $-R^{24}{}_2Si-$, $-O-$, $-S-$, or $-R^{24}N-$; $R^{24}$ represents a hydrogen atom, or a hydrocarbon group having from 1 to 20 carbon atoms; and m is an integer of from 0 to 4.

* * * * *